US011045193B2

(12) United States Patent
Schings et al.

(10) Patent No.: US 11,045,193 B2
(45) Date of Patent: Jun. 29, 2021

(54) ANVIL ASSEMBLY FOR LINEAR SURGICAL STAPLER

(71) Applicant: ETHICON LLC, Guaynabo, PR (US)

(72) Inventors: Brian D. Schings, Cincinnati, OH (US); Gary S. Jaworek, Cincinnati, OH (US); Donald J. Vogel, Lebanon, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 177 days.

(21) Appl. No.: 16/157,599

(22) Filed: Oct. 11, 2018

(65) Prior Publication Data

US 2020/0113561 A1 Apr. 16, 2020

(51) Int. Cl.
| | |
|---|---|
| *A61B 17/072* | (2006.01) |
| *A61B 17/11* | (2006.01) |
| *A61B 17/115* | (2006.01) |
| *A61B 17/00* | (2006.01) |
| *B29C 45/14* | (2006.01) |
| *B29L 31/00* | (2006.01) |

(52) U.S. Cl.
CPC .......... *A61B 17/072* (2013.01); *A61B 17/115* (2013.01); *A61B 17/1114* (2013.01); *A61B 2017/00367* (2013.01); *A61B 2017/00526* (2013.01); *A61B 2017/0725* (2013.01); *A61B 2017/07214* (2013.01); *A61B 2017/07257* (2013.01); *A61B 2017/07264* (2013.01); *A61B 2017/07271* (2013.01); *A61B 2017/07278* (2013.01); *A61B 2017/07285* (2013.01); *B29C 45/14* (2013.01); *B29L 2031/7546* (2013.01)

(58) Field of Classification Search
CPC ............ A61B 17/07207; A61B 17/068; A61B 17/072; A61B 2017/07214; A61B 2017/07257
USPC ................................ 227/176.1, 175.1, 175.3
See application file for complete search history.

(56) References Cited

U.S. PATENT DOCUMENTS

| | | | |
|---|---|---|---|
| 4,272,002 A | * 6/1981 | Moshofsky | .......... A61B 17/072 227/135 |
| 4,991,764 A | 2/1991 | Mericle | |

(Continued)

FOREIGN PATENT DOCUMENTS

| | | |
|---|---|---|
| CN | 103 169 516 A | 6/2013 |
| EP | 0061466 A1 | 10/1982 |

(Continued)

OTHER PUBLICATIONS

European Search Report, Partial, and Provisional Written Opinion dated Jan. 7, 2020 for Application No. EP 19202542.7, 13 pgs.

(Continued)

*Primary Examiner* — Valentin Neacsu
(74) *Attorney, Agent, or Firm* — Frost Brown Todd LLC

(57) ABSTRACT

A surgical stapler includes a first stapler half a second stapler half configured to releasably couple together. The second stapler half includes a first elongate member, a second elongate member, and a polymeric body that encapsulates at least a portion of each of the first elongate member and the second elongate member. One of the first stapler half or the second stapler half includes a distal portion configured to receive a staple cartridge, and the other of the first stapler half or the second stapler half includes a distal portion having a plurality of staple-forming pockets.

20 Claims, 28 Drawing Sheets

(56) References Cited

U.S. PATENT DOCUMENTS

| | | | |
|---|---|---|---|
| 5,141,144 A | | 8/1992 | Foslien |
| 5,395,034 A | * | 3/1995 | Allen ............... A61B 17/07207 227/178.1 |
| 5,452,836 A | * | 9/1995 | Huitema ............. A61B 17/072 227/176.1 |
| 5,636,779 A | | 6/1997 | Palmer |
| 5,651,491 A | * | 7/1997 | Heaton ............ A61B 17/07207 227/175.1 |
| 5,792,135 A | | 8/1998 | Madhani et al. |
| 5,817,084 A | | 10/1998 | Jensen |
| 5,878,193 A | | 3/1999 | Wang et al. |
| 5,911,352 A | | 6/1999 | Racenet et al. |
| 6,155,473 A | * | 12/2000 | Tompkins ........ A61B 17/07207 227/175.2 |
| 6,231,565 B1 | | 5/2001 | Tovey et al. |
| 6,364,888 B1 | | 4/2002 | Niemeyer et al. |
| 6,783,524 B2 | | 8/2004 | Anderson et al. |
| 7,524,320 B2 | | 4/2009 | Tierney et al. |
| 7,691,098 B2 | | 4/2010 | Wallace et al. |
| 7,806,891 B2 | | 10/2010 | Nowlin et al. |
| 7,905,381 B2 | | 3/2011 | Baxter, III et al. |
| 7,954,686 B2 | | 6/2011 | Baxter, III et al. |
| 8,348,129 B2 | | 1/2013 | Bedi et al. |
| 8,479,969 B2 | | 7/2013 | Shelton, IV |
| 8,523,041 B2 | | 9/2013 | Ishitsuki et al. |
| 8,573,461 B2 | | 11/2013 | Shelton, IV et al. |
| 8,573,465 B2 | | 11/2013 | Shelton, IV |
| 8,602,288 B2 | | 12/2013 | Shelton, IV et al. |
| 8,616,431 B2 | | 12/2013 | Timm et al. |
| 8,783,541 B2 | | 7/2014 | Shelton, IV et al. |
| 8,789,740 B2 | | 7/2014 | Baxter, III et al. |
| 8,800,838 B2 | | 8/2014 | Shelton, IV |
| 8,820,605 B2 | | 9/2014 | Shelton, IV |
| 8,844,789 B2 | | 9/2014 | Shelton, IV et al. |
| 9,155,537 B2 | | 10/2015 | Katre et al. |
| 9,301,759 B2 | | 4/2016 | Spivey et al. |
| 9,402,629 B2 | | 8/2016 | Ehrenfels et al. |
| 9,539,007 B2 | | 1/2017 | Dhakad et al. |
| 9,724,095 B2 | | 8/2017 | Gupta et al. |
| 2005/0159778 A1 | * | 7/2005 | Heinrich ............... A61B 17/072 606/216 |
| 2007/0167960 A1 | * | 7/2007 | Roth ................... A61B 17/072 606/153 |
| 2009/0308907 A1 | | 12/2009 | Nalagatla et al. |
| 2015/0018875 A1 | | 1/2015 | Knodel |
| 2015/0034695 A1 | | 2/2015 | Kapadia |
| 2015/0327855 A1 | | 11/2015 | Katre |
| 2016/0135811 A1 | | 5/2016 | Gupta et al. |
| 2016/0249920 A1 | * | 9/2016 | Gupta ................. A61B 17/072 227/180.1 |
| 2016/0262756 A1 | | 9/2016 | Patankar et al. |
| 2016/0310136 A1 | | 10/2016 | Gupta et al. |
| 2016/0338701 A1 | | 11/2016 | Patankar et al. |
| 2016/0338702 A1 | * | 11/2016 | Ehrenfels ............. A61B 17/105 |
| 2017/0079652 A1 | | 3/2017 | Dhakad et al. |
| 2017/0143335 A1 | | 5/2017 | Gupta et al. |
| 2017/0143336 A1 | | 5/2017 | Shah et al. |
| 2017/0325811 A1 | * | 11/2017 | Gupta ................. A61B 17/064 |

FOREIGN PATENT DOCUMENTS

| | | |
|---|---|---|
| EP | 0178941 B1 | 4/1986 |
| EP | 0677273 B1 | 10/1995 |
| EP | 1702567 B1 | 9/2006 |
| EP | 2532312 B1 | 12/2012 |
| EP | 3065649 A1 | 9/2016 |
| EP | 2741685 B1 | 1/2017 |
| EP | 3155988 A1 | 4/2017 |
| EP | 2804541 B1 | 10/2017 |
| WO | WO 2017056028 A1 | 4/2017 |
| WO | WO 2018/044669 A1 | 3/2018 |

OTHER PUBLICATIONS

European Search Report, Extended, and Written Opinion dated Jun. 25, 2020 for Application No. EP 19202542.7, 12 pgs.

International Search Report and Written Opinion dated Mar. 19, 2020 for Application PCT/IB2019/058687, 17 pgs.

U.S. Appl. No. 15/889,363, entitled "Release Mechanism for Linear Surgical Stapler," filed Feb. 6, 2018.

U.S. Appl. No. 15/889,370, entitled "Lockout Assembly for Linear Surgical Stapler," filed Feb. 6, 2018.

U.S. Appl. No. 15/889,374, entitled "Features to Align and Close Linear Surgical Stapler," filed Feb. 6, 2018.

U.S. Appl. No. 15/889,376, entitled "Releasable Coupling Features for Proximal Portions of Linear Surgical Stapler," filed Feb. 6, 2018.

U.S. Appl. No. 15/889,388, entitled "Firing Lever Assembly for Linear Surgical Stapler," filed Feb. 6, 2018.

U.S. Appl. No. 15/889,390, entitled "Clamping Mechanism for Linear Surgical Stapler," filed Feb. 6, 2018.

U.S. Appl. No. 16/102,164, entitled "Firing System for Linear Surgical Stapler," filed Aug. 13, 2018.

U.S. Appl. No. 16/102,170, entitled "Clamping Assembly for Linear Surgical Stapler," filed Aug. 13, 2018.

U.S. Appl. No. 16/157,605, entitled "Closure Assembly for Linear Surgical Stapler," filed Oct. 11, 2018.

U.S. Appl. No. 16/165,587, entitled "Decoupling Mechanism for Linear Surgical Stapler," filed Oct. 19, 2018.

* cited by examiner

ANVIL ASSEMBLY FOR LINEAR SURGICAL STAPLER

BACKGROUND

In some surgical operations, such as a gastrointestinal anastomosis, it may be desirable to clamp down on one or more layers of tissue, cut through the clamped layers, and simultaneously drive staples through the layers to substantially seal the severed layers of tissue together near their severed ends. One such instrument that may be used in such operations is a linear surgical stapler, also referred to as a "linear cutter." A linear surgical stapler generally includes a first half (referred to as a "cartridge half" or "reload half") having a distal jaw configured to support a staple cartridge (or "reload"), and a second half (referred to as an "anvil half") having a distal jaw that supports an anvil surface having staple-forming features. The stapler further includes a moveable clamp lever configured to releasably clamp the stapler halves together. The stapler halves are configured to pivot relative to one another to receive and clamp tissue between the two distal jaws when the clamp lever is closed. A firing assembly of the stapler is configured to be actuated to cut the clamped layers and simultaneously drive staples through the tissue on either side of the cut line. After firing the stapler, the clamp lever may be opened and the stapler halves separated to release the severed and stapled tissue.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
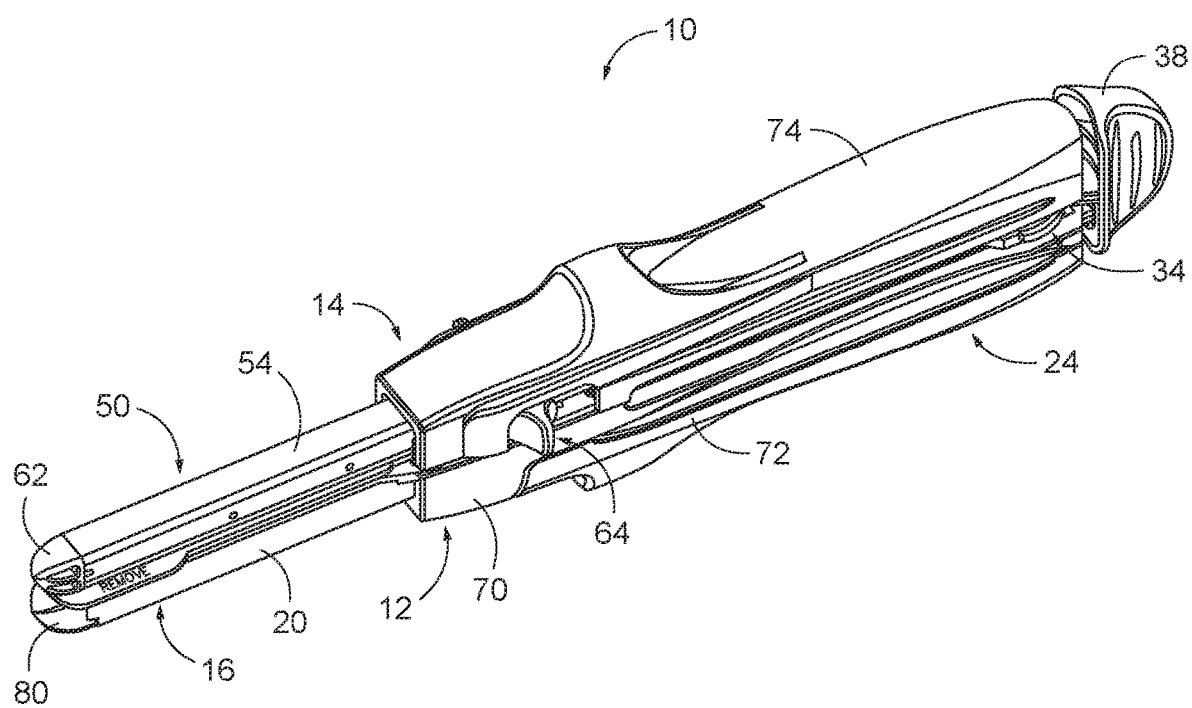
FIG. 1 depicts a distal perspective view of an exemplary linear surgical stapler, showing a cartridge half and an anvil half of the stapler coupled together with a clamp lever of the cartridge half in a fully closed position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Linear Surgical Stapler

A. Overview of Linear Surgical Stapler

Figure 2:
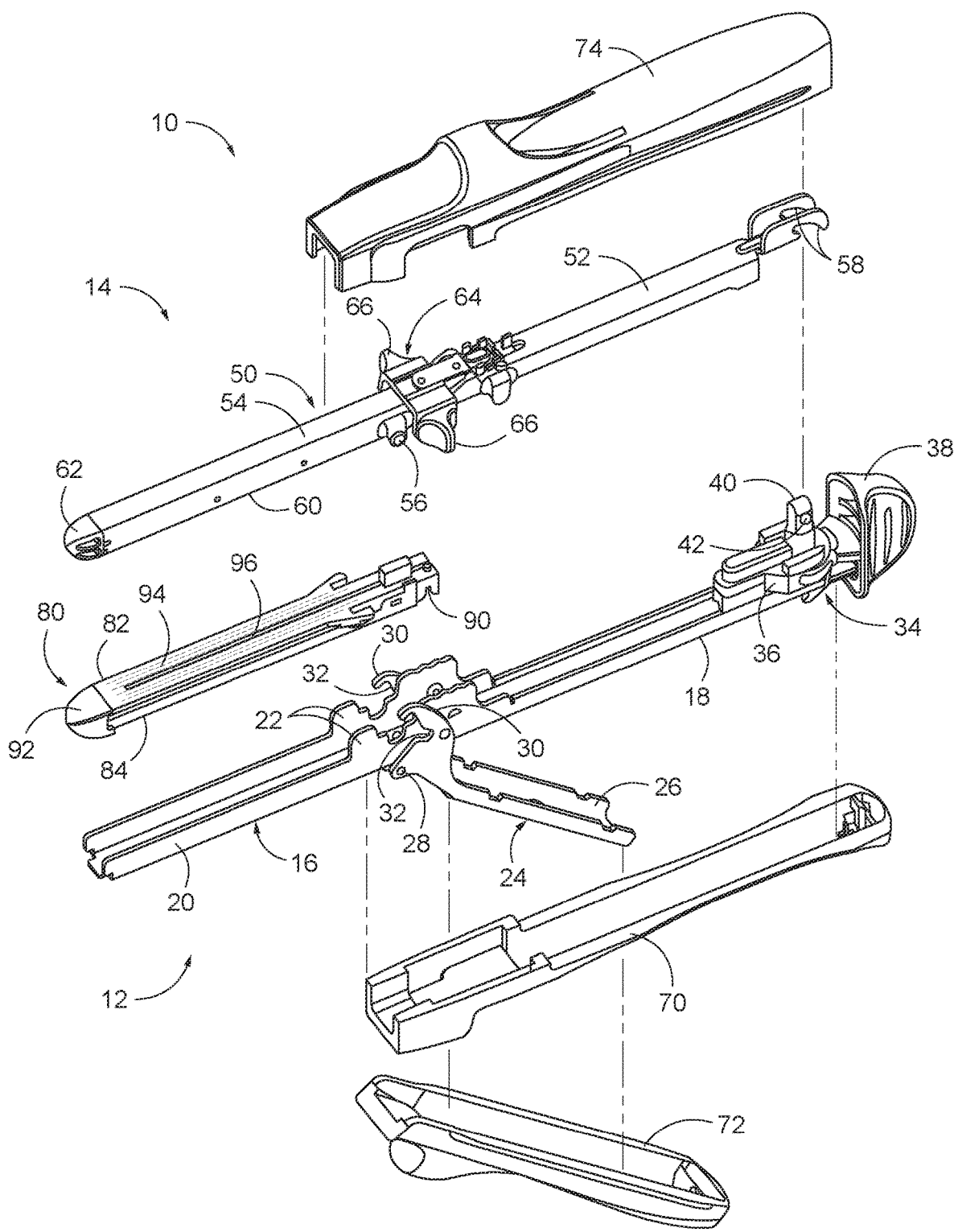
FIG. 2 depicts an exploded perspective view of the linear surgical stapler of FIG. 1.

FIGS. 1 and 2 show an exemplary linear surgical stapler (10) (also referred to as a "linear cutter") suitable for use in a variety of cutting and stapling procedures, such as a gastrointestinal anastomosis procedure. Linear surgical stapler (10) includes a cartridge half (12) (also referred to as a "reload half") and an anvil half (14) configured to releasably couple together to clamp tissue therebetween. Cartridge half (12) includes an elongate cartridge channel (16) having a proximal frame portion (18) that slidably retains a portion of a firing assembly (34), a distal jaw portion (20) that supports a staple cartridge (80) (or "reload"), and a pair of upright side flanges (22) arranged medially therebetween.

Cartridge half (12) further includes a clamp lever (24) pivotably coupled to an underside of cartridge channel (16) in approximate alignment with side flanges (22). Clamp lever (24) includes an elongate lever arm (26) having a free proximal end and a distal end that is pivotably coupled to cartridge channel (16) with a pivot pin (28). A pair of opposed jaws (30) (also referred to as "hook latches") extend distally from the distal end of lever arm (26) alongside flanges (22) of cartridge channel (16). Each jaw (30) includes a respective elongate slot (32) having a closed proximal end and an open distal end, and which defines upper and lower camming surfaces configured to engage a respective latch projection (56) of anvil half (14). As described below, clamp lever (24) is operable to pivot relative to cartridge channel (16) between open and closed positions to releasably clamp anvil half (14) against cartridge half (12) and thereby capture tissue layers therebetween.

As shown best in FIG. 2, firing assembly (34) of cartridge half (12) includes a slider block (36) slidably retained within proximal frame portion (18) of cartridge channel (16), an actuator (38) (or "firing knob") movably coupled with slider block (36), and an elongate actuating beam (not shown) extending distally from slider block (36) and configured to couple with a sled (100) (see FIG. 3) housed within staple cartridge (80). Actuator (38) of the present example is configured to pivot about the proximal end of cartridge half (12) to provide for "dual-sided firing" of stapler (10). Specifically, actuator (38) may be positioned along either lateral side of cartridge half (12) to perform a distal firing stroke, such that stapler (10) may be conveniently fired in a variety of orientations during a surgical procedure.

Figure 5A:
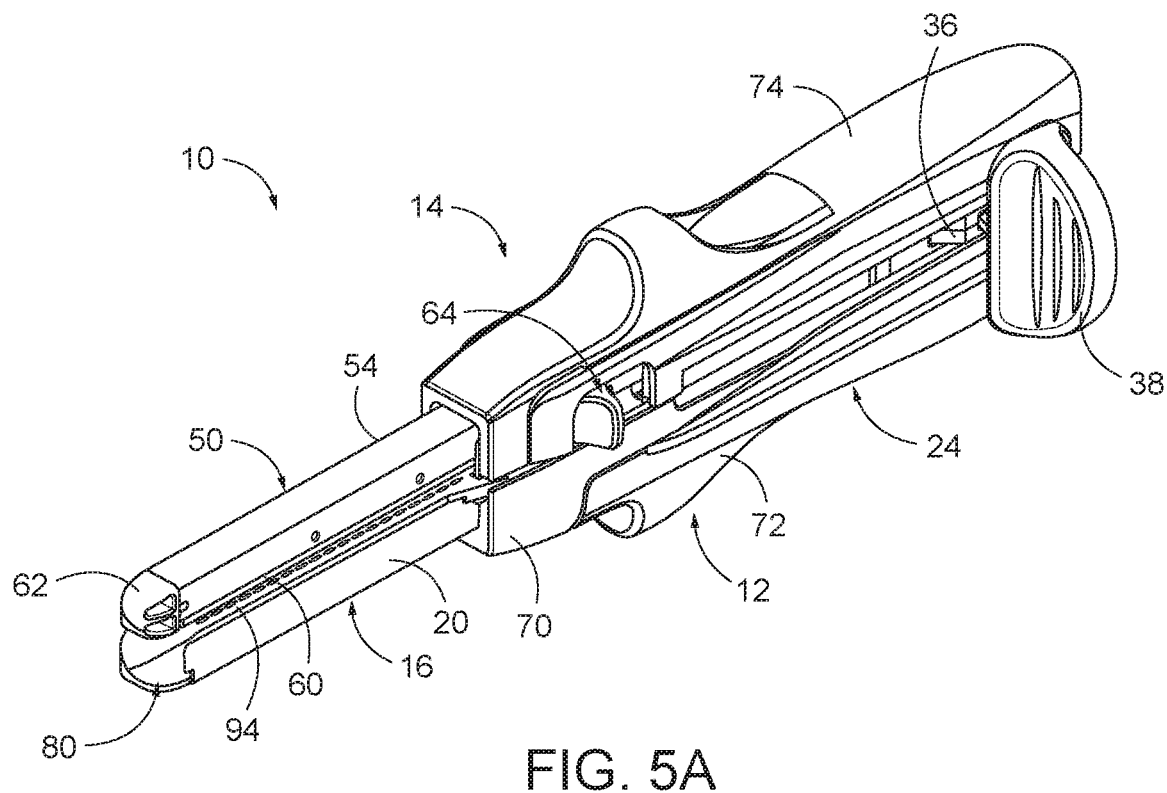
FIG. 5A depicts a distal perspective view of the linear surgical stapler of FIG. 1, showing an actuator of the stapler in a proximal, pre-fired position.
Figure 5B:
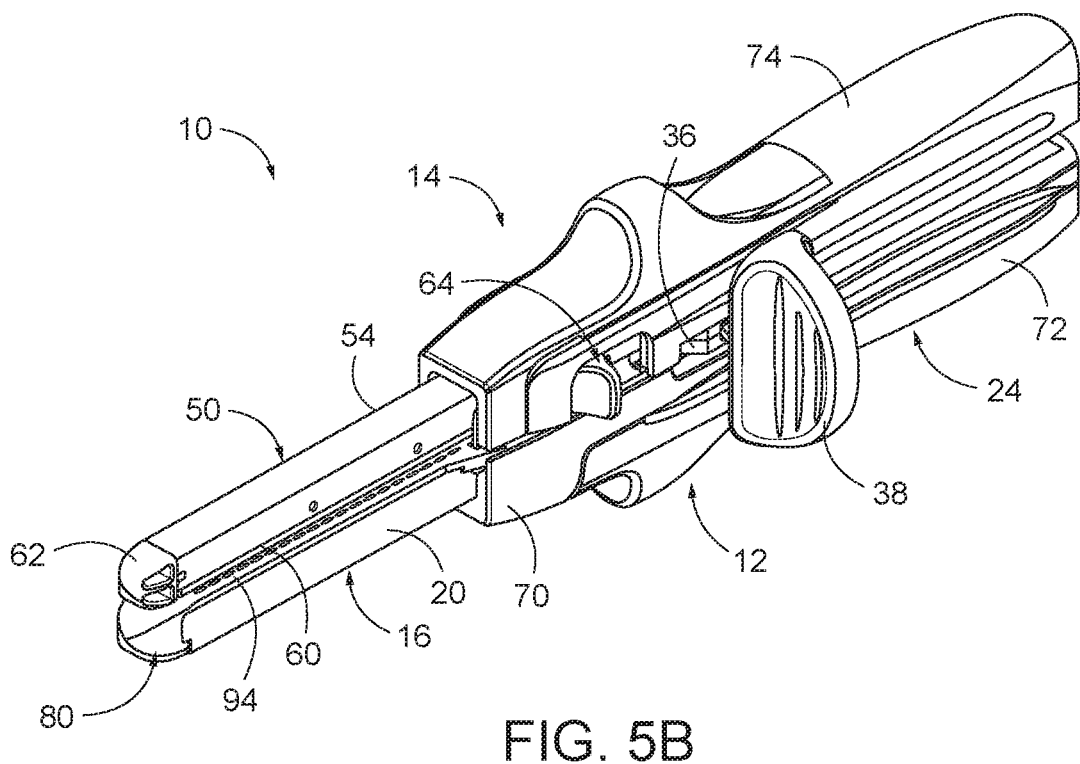
FIG. 5B depicts a distal perspective view of the linear surgical stapler of FIG. 1, showing the actuator in a distal, fired position.

Slider block (36) is configured to be translatably driven within proximal frame portion (18) by actuator (38) between a proximal home position shown in FIGS. 2 and 5A, and a distal fired position shown in FIG. 5B. In the proximal home position, slider block (36) abuts a post (40) fixed at a proximal end of cartridge channel (16). A free end of post (40) supports a laterally extending pivot pin (42). As described below, actuator (38) may be driven distally when stapler halves (12, 14) are fully coupled together and clamp lever (24) is closed. Distal advancement of actuator (38) along either lateral side of stapler (10) drives slider block (36) and the elongate actuating beam distally, which in turn drives sled (100) distally through staple cartridge (80). As described below, distal translation of sled (100) through staple cartridge (80) provides for simultaneous stapling and cutting of tissue clamped between stapler halves (12, 14).

As shown best in FIGS. 1 and 2, anvil half (14) of linear surgical stapler (10) includes an elongate anvil channel (50) having a proximal frame portion (52) and a distal jaw portion (54). Anvil channel (50) further includes a latch feature in the form of a pair of projections (56) that extend transversely from a medial portion of anvil channel (50) in a direction toward cartridge half (12). Each latch projection (56) may include a circular rotating cap configured to be captured within the slot (32) of a respective clamp lever jaw (30) when anvil half (14) is coupled with cartridge half (12) and clamp lever (24) is pivoted from the open position to the closed position, as described below. A pair of hooks (58) extend proximally from a proximal end of frame portion (52) and are configured to releasably capture opposed lateral ends of proximal pivot pin (42) of cartridge half (12). Distal jaw portion (54) supports an anvil surface in the form of an anvil plate (60) having a plurality of staple-forming pockets (not shown), and additionally supports a distal tip member (62). In other versions of stapler (10), the anvil surface may be formed integrally with or otherwise be rigidly connected to distal jaw portion (54) of anvil channel (50). In the present version, each of anvil channel (50) and cartridge channel (16) is a monolithic structure formed of a metal, such as stainless steel, that provides rigidity to the respective stapler half (12, 14).

Anvil half (14) of the present example further includes a staple height adjustment mechanism (64) mounted to a medial portion of anvil channel (50). Staple height adjustment mechanism (64) is operatively coupled with anvil plate (60), for example via one or more camming features (not shown), and includes a pair of user-engageable projections (66). Longitudinal adjustment of projections (66) between a plurality of predetermined positions causes anvil plate (60) to move transversely relative to distal jaw portion (54) of anvil channel (50). This enables adjustment of a transverse gap distance between anvil plate (60) and a deck (94) of staple cartridge (80) that defines the height of staples being formed. A larger gap distance, and thus a greater staple height, may be set when stapling tissues of greater thicknesses. Conversely, a smaller gap distance, and thus a smaller staple height, may be set when stapling tissues of lesser thicknesses. It will be appreciated that staple height adjustment mechanism (64) may be omitted in some versions, in which case the anvil surface may be fixed relative to anvil channel (50). For instance, the anvil surface may be formed integrally with or otherwise fixedly secured to distal jaw portion (54).

As shown best in FIGS. 1 and 2, linear surgical stapler (10) further includes a plurality of shrouds (70, 72, 74) that cover select portions of stapler (10) and promote effective grip and manipulation of stapler (10) by an operator during use. In the present example, cartridge half (12) includes a first shroud (70) that covers an outwardly facing side of proximal frame portion (18) of cartridge channel (16). Cartridge half (12) further includes a second shroud (72) that covers an outwardly facing side of clamp lever (24) and is configured to pivot with clamp lever (24) relative to cartridge channel (16) and first shroud (70). Anvil half (14) includes a third shroud (74) that covers an outwardly facing side of proximal frame portion (52) of anvil channel (50), including proximal hooks (58). Each shroud (70, 72, 74) may be coupled with its respective components of stapler (10) by any suitable means apparent to those of ordinary skill in the art. Additionally, each shroud (70, 72, 74) may be formed of one or more materials and be provided with texturing suitable to promote effective gripping of the shroud (70, 72, 74) by an operator to enable safe and efficient use of stapler (10) during a surgical procedure.

Figure 3:
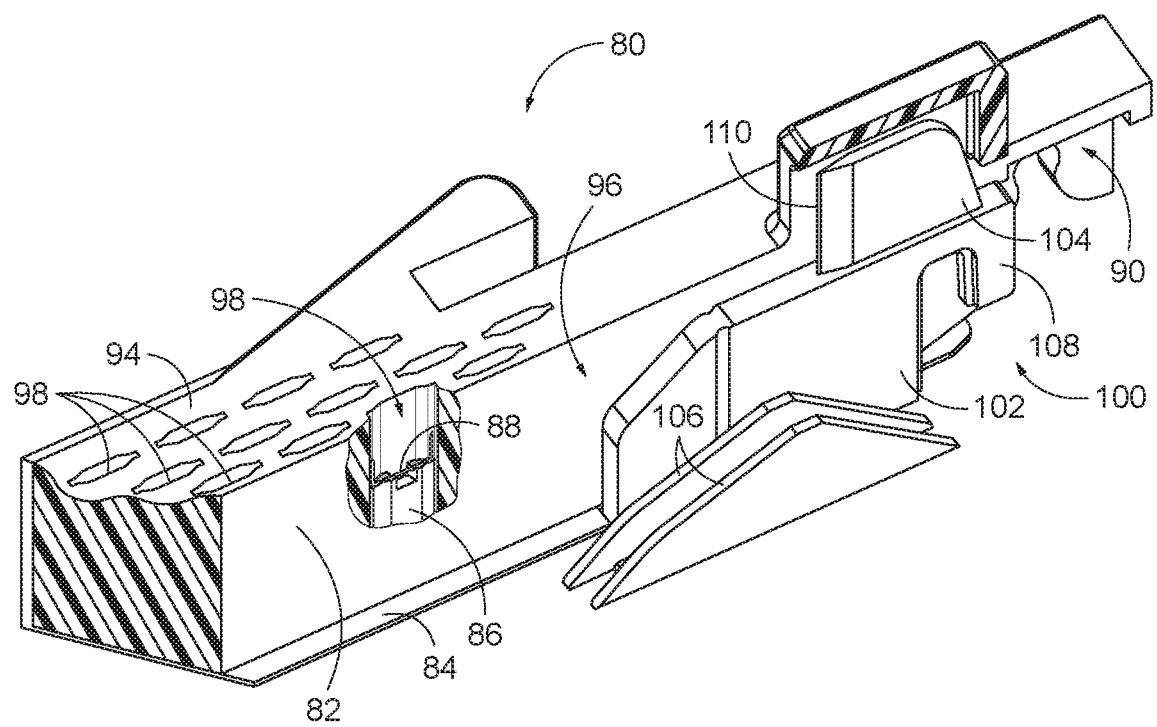
FIG. 3 depicts a cross-sectional perspective view of a staple cartridge assembly of the linear surgical stapler of FIG. 1.

As shown in FIGS. 2 and 3, staple cartridge (80) of the present example is an assembly that comprises a cartridge body (82), a pan (84) that covers an open lower side of cartridge body (82), and a plurality of staple drivers (86) housed within cartridge body (82) and each being configured to drive a respective staple (88). Cartridge body (82) includes a proximal end having coupling features (90) configured to releasably engage corresponding coupling features (not shown) of distal jaw portion (20) of cartridge channel (16), and a distal end defining a tapered nose (92). An upper side of cartridge body (82) defines a generally planar deck (94) through which a longitudinal slot (96) and a plurality of staple cavities (98) open. Each staple cavity (98) houses a respective staple driver (86) and a staple (88). As shown in FIG. 3, an interior of cartridge body (82) slidably houses a sled (100) that comprises a sled body (102) and knife member (104). Lateral sides of sled body (102) support a plurality of cam ramps (106) that taper distally. A proximal end of sled body (102) includes a downwardly extending tab (108) configured to lockingly engage a distal end of the elongate actuating beam (or "knife pusher") (not shown) of firing assembly (34) when staple cartridge (80) is mounted to cartridge half (12) of stapler (10). Knife member (104) extends upwardly from an upper side of sled body (102) and presents a distally facing cutting edge (110) configured to cut tissue.

Sled (100) is configured to translate distally through cartridge body (82) in response to distal actuation of firing assembly (34), such that knife member (104) translates distally through longitudinal slot (96) to cut tissue clamped between stapler halves (12, 14). Simultaneously, cam ramps (106) translate distally through respective interior slots (not shown) of cartridge body (82) to actuate staple drivers (86) and staples (88) upwardly through staple cavities (98) so that free ends of staples (88) pierce through the clamped tissue and deform against staple-forming pockets of anvil plate (60). In this manner, distal actuation of firing assembly (34)

provides for simultaneous severing and stapling of tissue clamped between the distal end effector portions of stapler halves (12, 14).

Linear surgical stapler (10) and staple cartridge (80) may be further configured and operable in accordance with one or more teachings of U.S. Pat. No. 7,905,381, entitled "Surgical Stapling Instrument with Cutting Member Arrangement," issued Mar. 15, 2011; U.S. Pat. No. 7,954,686, entitled "Surgical Stapler with Apparatus for Adjusting Staple Height," issued Jun. 7, 2011; U.S. Pat. No. 8,348,129, entitled "Surgical Stapler Having A Closure Mechanism," issued Jan. 8, 2013; and/or U.S. Pat. No. 8,789,740, entitled "Linear Cutting and Stapling Device with Selectively Disengageable Cutting Member," issued Jul. 29, 2014. The disclosure of each of these references is incorporated by reference herein.

B. Exemplary Use of Linear Surgical Stapler

Figure 4A:
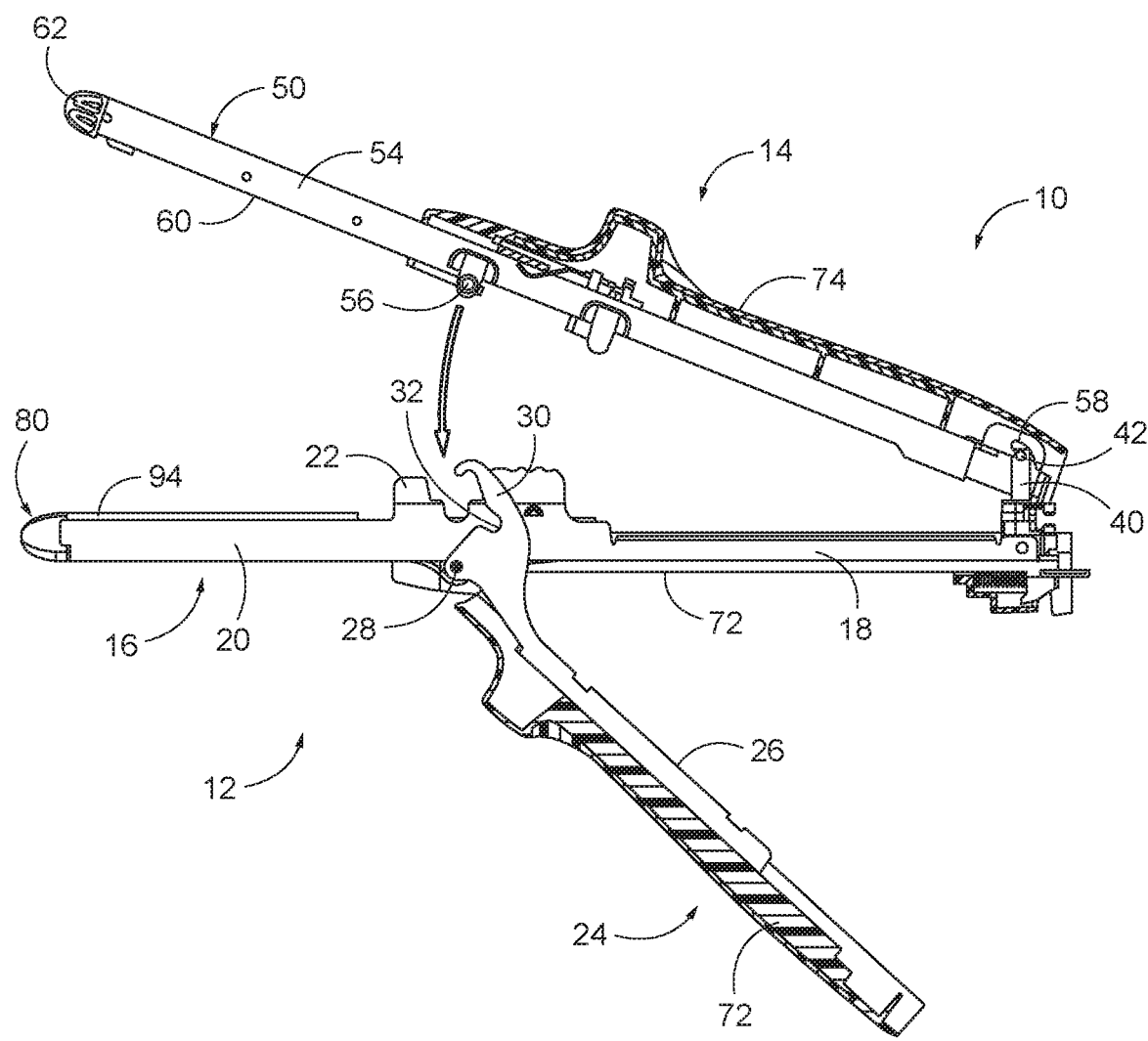
FIG. 4A depicts a cross-sectional side view of the linear surgical stapler of FIG. 1, showing the stapler halves coupled together at their proximal ends with the clamp lever in an open position.
Figure 4B:
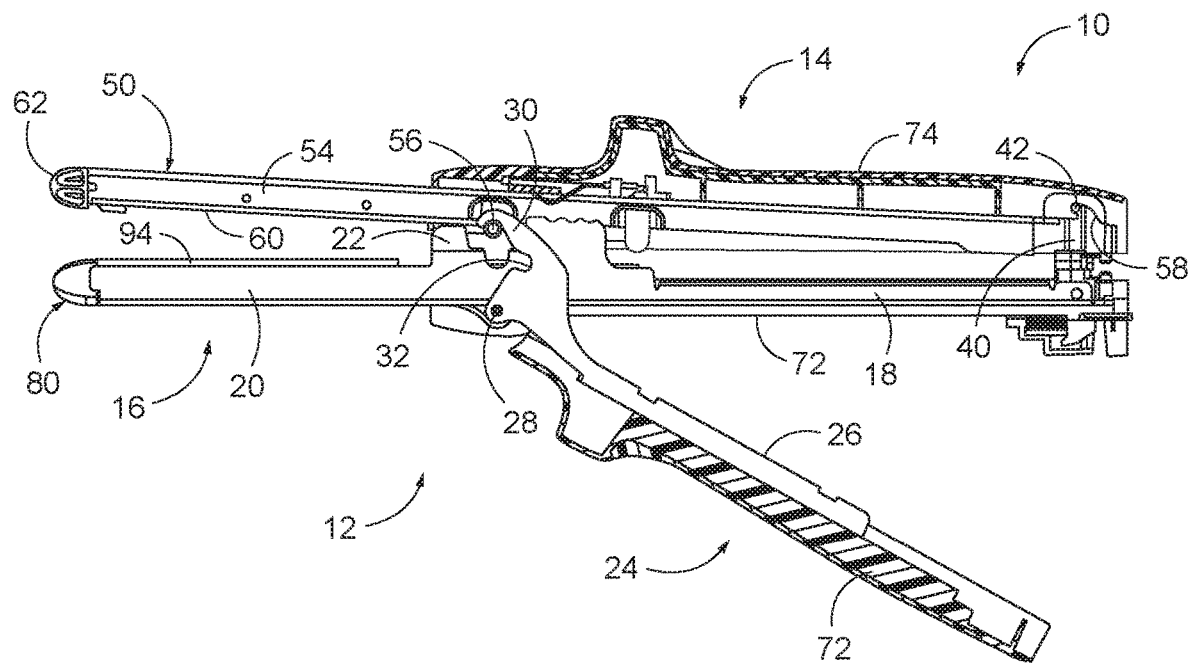
FIG. 4B depicts a cross-sectional side view of the linear surgical stapler of FIG. 1, showing the stapler halves coupled together with the clamp lever in a partially closed position.
Figure 4C:
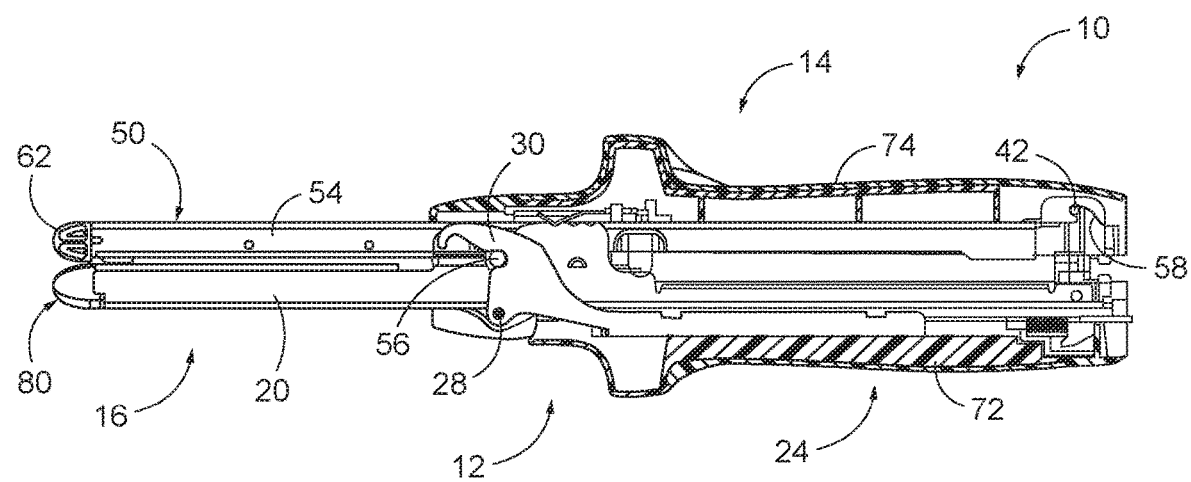
FIG. 4C depicts a cross-sectional side view of the linear surgical stapler of FIG. 1, showing the stapler halves coupled together with the clamp lever in a fully closed position.

FIGS. 4A-4C show exemplary coupling of stapler halves (12, 14) during a surgical procedure. As shown in FIG. 4A, the proximal end of anvil half (14) is aligned with the proximal end of cartridge half (12) such that proximal pivot pin (42) of cartridge half (12) is received by proximal hooks (58) of anvil half (14). With clamp lever (24) in the open position, anvil half (14) is then pivoted toward cartridge half (12), about proximal pivot pin (42), to direct latch projections of anvil half (14) into slots (32) of clamp lever jaws (30). Once latch projections (56) are received by clamp lever jaws (30), clamp lever (24) is pivoted toward the partially closed position shown in FIG. 4B. In this partially closed position of clamp lever (24), anvil half (14) is partially clamped with cartridge half (12) such that stapler (10) may now be held with a single hand without halves (12, 14) undesirably separating from one another. Additionally, in this state, the distal portions of stapler halves (12, 14) remain spaced apart from one another to permit positioning of tissue between the distal portions. It will be appreciated that tissue may be positioned between the distal portions of stapler halves (12, 14) before or upon achieving this partially clamped state.

As shown in FIG. 4C, clamp lever (24) is then pivoted further toward its fully closed position such that the camming surfaces of clamp lever jaws (30) draw latch projections of anvil half (14) proximally against the closed proximal ends of slots (32) of clamp lever jaws (30), thereby fully clamping stapler halves (12, 14) together with tissue positioned securely therebetween. Once halves (12, 14) of stapler (10) are in a fully clamped state, actuator (38) may be manipulated to fire staple cartridge (80). In particular, as shown in FIGS. 5A and 5B, actuator (38) is pivoted about the proximal end of stapler (10) to overlie one of the lateral sides of stapler (10). Actuator (38) is then driven distally to actuate firing assembly (34) in the manner described above and thereby simultaneously sever and staple the clamped tissue. Upon completing a distal firing stroke, actuator (38) may be returned to its proximal home position shown in FIG. 2, and clamp lever (24) may then be opened to separate stapler halves (12, 14) from one another and release the stapled and severed tissue.

II. Exemplary Stapler Halves Having Structural Plates and Molded Body

As described above, anvil half (14) of linear surgical stapler (10) includes a proximal frame portion (52) and a distal jaw portion (54) both defined by anvil channel (50), which is a monolithic structure formed entirely of metal. In some instances, it may be desirable to provide a linear surgical stapler half with an alternative configuration that enhances longitudinal stiffness and thus resistance to distal tip deflection, while minimizing weight and manufacturing costs of the stapler half. Each exemplary anvil half (200, 300, 400) described below in connection with FIGS. 6-25 presents a hybrid construction that comprises a pair of elongate inner structural members in the form of spine plates, and a polymeric body that is formed about and at least partially encapsulates the spine plates to provide an anvil half construction that is stiff, lightweight, and cost effective to manufacture. As described in greater detail in connection with FIGS. 26A-26B, the polymeric body of each exemplary anvil half (200, 300, 400) may be formed through an injection molding process, which may include overmolding and insert molding steps.

It will be appreciated that each exemplary anvil half (200, 300, 400) described below may be used with any suitable cartridge half to define a linear surgical stapler. For instance, anvil halves (200, 300, 400) may be used with cartridge half (12) described above or with cartridge halves (702, 802) described below. In other instances, anvil halves (200, 300, 400) may be used with any of the exemplary cartridge halves described in U.S. application Ser. No. 16/102,164, entitled "Firing System for Linear Surgical Stapler," filed on Aug. 13, 2018, issued as U.S. Pat. No. 10,898,187 on Jan. 26, 2021; U.S. application Ser. No. 16/102,170, entitled "Clamping Assembly for Linear Surgical Stapler," filed on Aug. 13, 2018, published as U.S. Pub. No. 2020/0046353 on Feb. 13, 2020; or U.S. App. Ser. No. 16/157,605, entitled "Closure Assembly for Linear Surgical Stapler," filed on Oct. 11, 2018, issued as U.S. Pat. No. 10,905,419 on Feb. 2, 2021, the disclosures of which are incorporated by reference herein. Moreover, while the exemplary hybrid constructions are shown and described herein in the context of anvil halves (200, 300, 400), it will be appreciated that such hybrid constructions may be applied to a cartridge half of a linear surgical stapler as well.

A. Exemplary Anvil Half Having Structural Plates with Raised Portions

Figure 6:
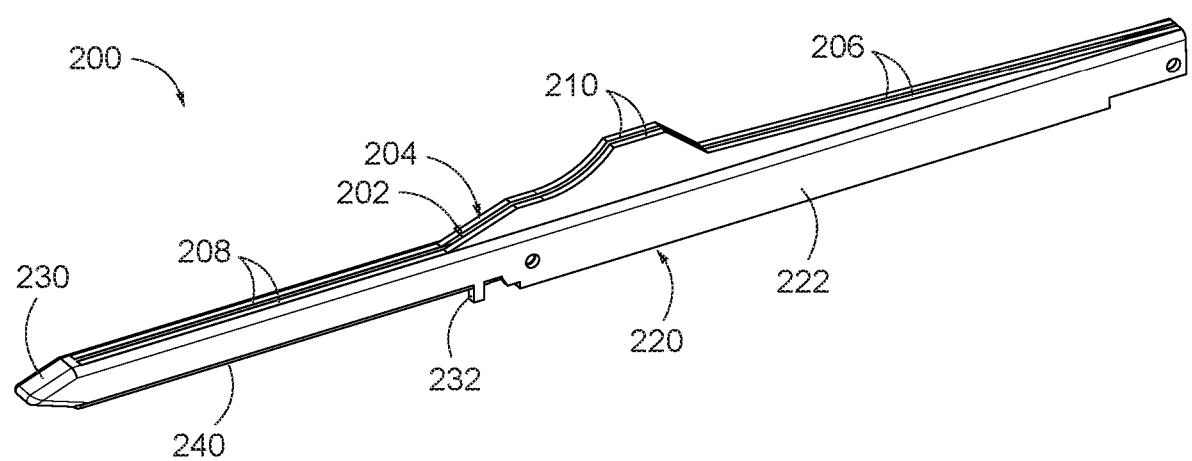
FIG. 6 depicts a perspective view of another exemplary anvil half of a linear surgical stapler, having a pair of spine plates, an anvil plate, and a body.

FIG. 6 shows an exemplary anvil half (200) having a pair of elongate inner structural members in the form spine plates (202, 204), a polymeric body (220) molded about spine plates (202, 204), and an anvil plate (240) coupled with distal portions of polymeric body (220) and spine plates (202, 204). Though not shown, anvil half (200) may further include a shroud, which may be similar to anvil shroud (74) described above, that covers outwardly facing surfaces of proximal portions of spine plates (202, 204) and polymeric body (220) to promote effective grip of anvil half (200) by a user.

Figure 7:
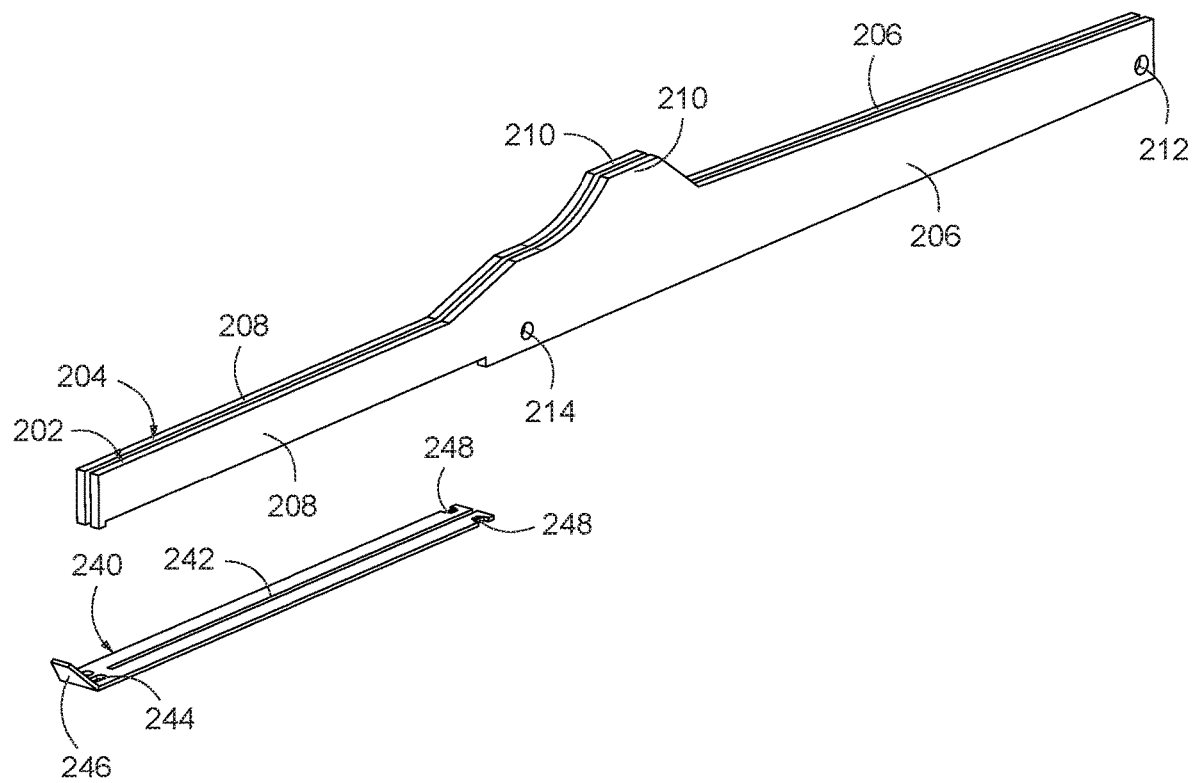
FIG. 7 depicts a perspective view of the spine plates and the anvil plate of the anvil half of FIG. 6, showing the anvil plate separated from the spine plates before the body is formed about the spine plates and the anvil plate.

As shown best in FIGS. 6 and 7, spine plates (202, 204) of the present example are spaced laterally from one another and are arranged parallel to and equidistantly from a longitudinal axis of anvil half (200), and transversely to a tissue clamping plane defined by anvil plate (240). Additionally, spine plates (202, 204) are formed from a suitably rigid material, such as stainless steel or a variety of other materials of similar or greater rigidity that will be apparent to those of ordinary skill in the art. It will be understood that such materials for spine plates (202, 204) may comprise non-polymeric materials such as metals in some versions, and polymeric materials in other versions. Such an orientation and construction of spine plates (202, 204) provides anvil half (200) with a support structure of suitable stiffness and resistance to tip deflection during clamping of tissue against anvil plate (240), while maintaining a simple and minimalistic configuration of the support structure that provides for a lightweight device that is cost effective to manufacture. While spine plates (202, 204) of the present example are identical in size and shape, spine plates (202, 204) may differ in size and/or shape in other examples.

Each spine plate (202, 204) of the present example includes an elongate proximal plate portion (206), an elongate distal plate portion (208), and a raised medial plate portion (210) arranged therebetween. Raised medial plate portions (210) are configured to align with and be received within a shoulder feature of an anvil shroud (not shown). Each spine plate (202, 204) further includes a proximal hole (212) arranged at a proximal end of proximal plate portion (206), and which is configured to receive a first projection (not shown) laterally therethrough. Each spine plate (202, 204) further includes a distal hole (214) arranged approximately at a distal end of medial plate portion (210), and which configured to receive a second projection (not shown) laterally therethrough. In some versions, such lateral projections may be in the form of pins, for example as disclosed in U.S. application Ser. No. 16/102,164, issued as U.S. Pat. No. 10,898,187 on Jan. 26, 2021 and U.S. application Ser. No. 16/102,170, published as U.S. Pub. No. 2020/0046353 on Feb. 13, 2020, incorporated by reference above, such that the pins extend laterally through spine plates (202, 204) and polymeric body (220). In other versions, one or both of such lateral projections may be defined by polymeric body (220). In use, the proximal lateral projection is configured to be releasably captured by a proximal end of a cartridge half, and the distal projection is configured to be releasably captured by a clamp lever of the cartridge half for clamping anvil half (200) against the cartridge half.

Figure 12:
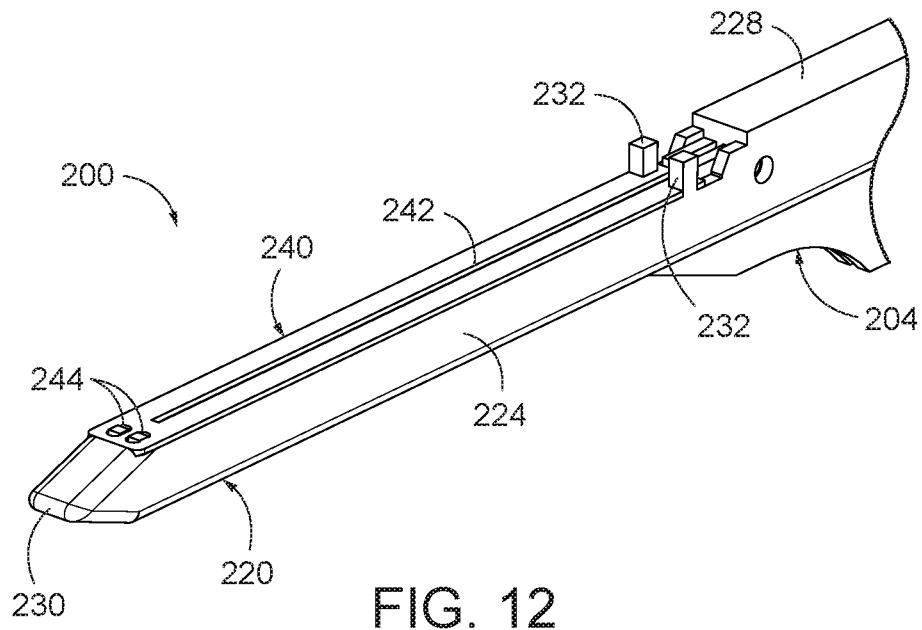
FIG. 12 depicts a perspective view of a distal portion of the anvil half of FIG. 6, showing the anvil half oriented such that the anvil plate faces upwardly.

As shown in FIGS. 7 and 12, anvil plate (240) includes a longitudinal slot (242) configured to slidably receive a knife member (not shown) therethrough, and an anvil surface having a plurality of staple-forming pockets (not shown) configured to deform staples ejected by a staple cartridge (not shown). Such stapler-forming pockets may be similar to pockets (906a, 906b) of anvil plate (900) described below. Anvil plate (240) is oriented transversely to spine plates (202, 204) such that anvil plate (240) is supported by and spans laterally across lower edges of elongate distal plate portions (208) of spine plates (202, 204). As described below, anvil plate (240) of the present example includes additional features that enables polymeric body (220) to securely attach to anvil plate (240) during the molding process of polymeric body (220). In some versions of anvil half (200), anvil plate (240) may be omitted, and the anvil surface and staple-forming pockets may be provided by a corresponding surface of polymeric body (220).

Figure 8:
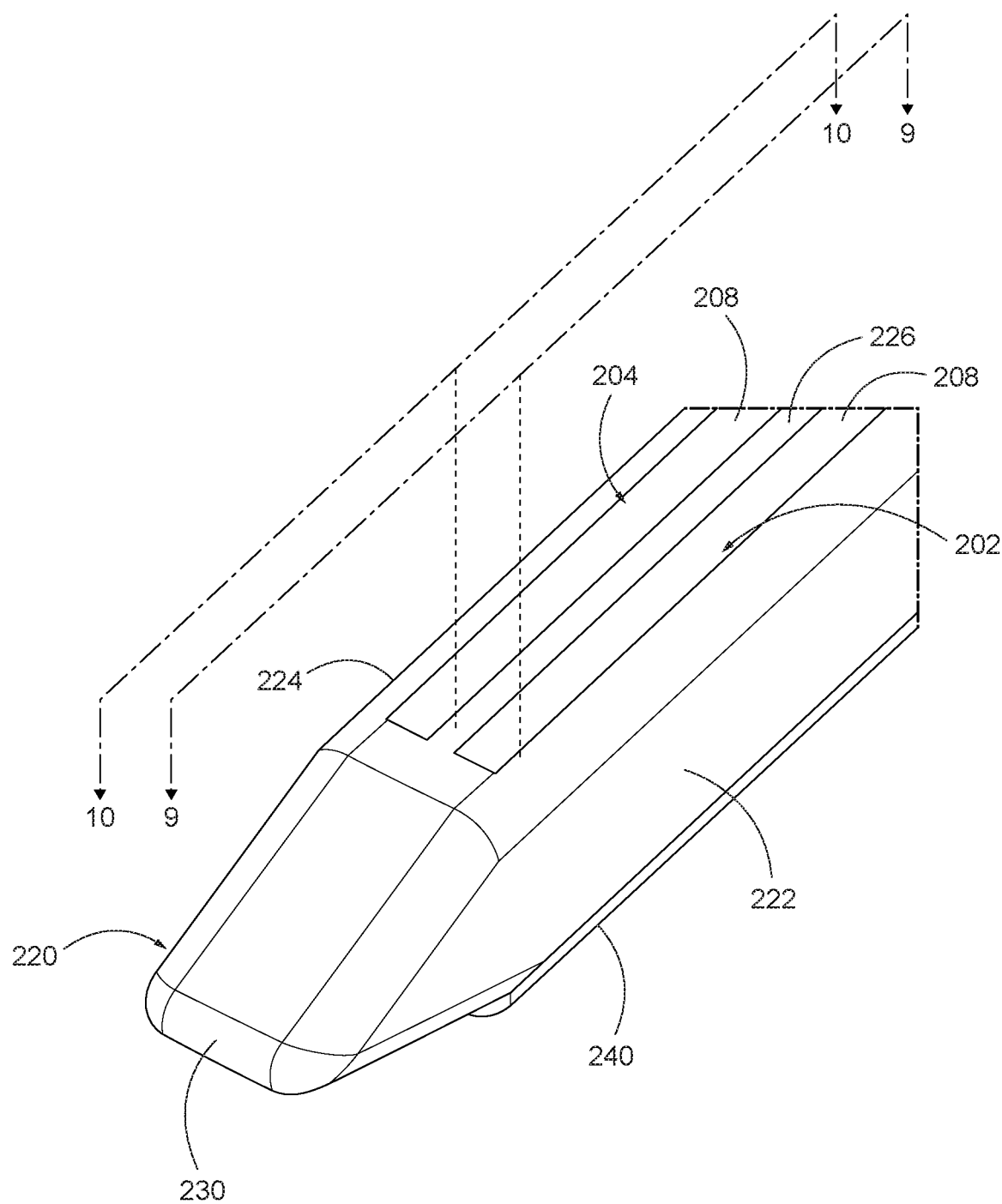
FIG. 8 depicts a perspective view of a distal portion of the anvil half of FIG. 6.
Figure 9:
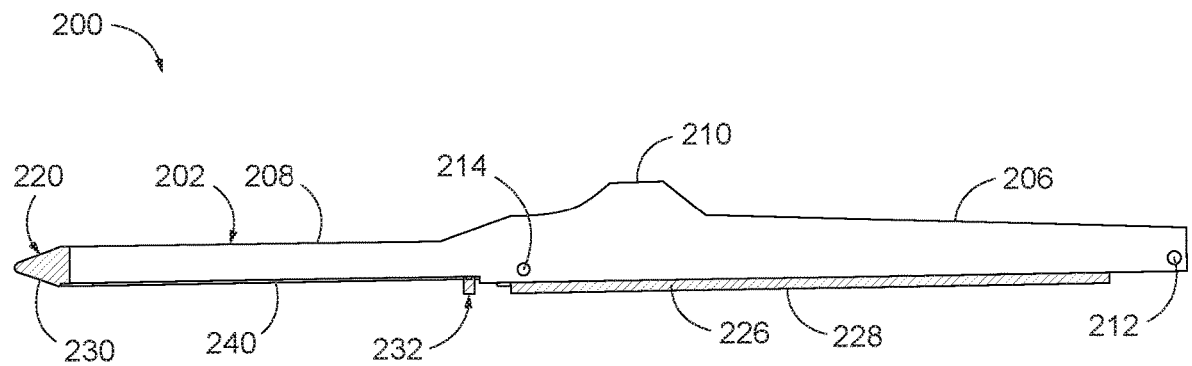
FIG. 9 depicts a side cross-sectional view of the anvil half of FIG. 6, taken along section line 9-9 in FIG. 8.
Figure 10:
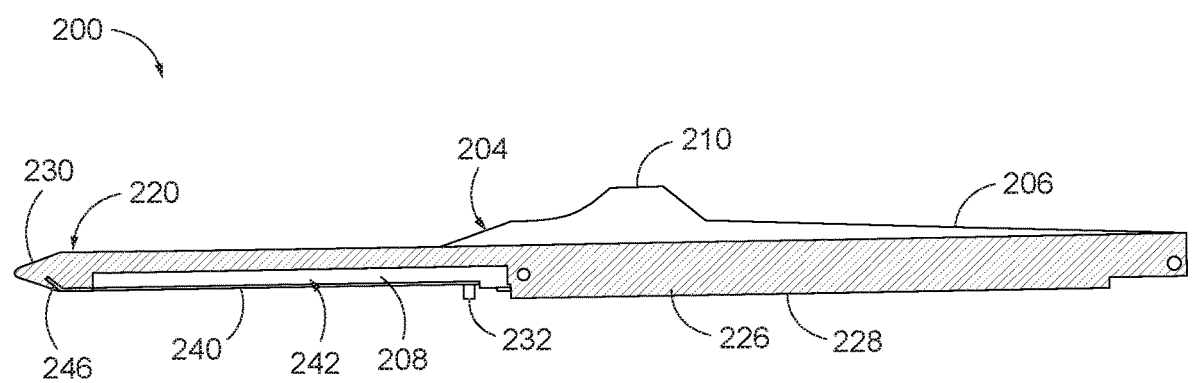
FIG. 10 depicts a side cross-sectional view of the anvil half of FIG. 6, taken along section line 10-10 in FIG. 8.

As shown in FIGS. 8-10, polymeric body (220) is a monolithic structure formed about spine plates (202, 204) so as to encapsulate at least a portion of each spine plate (202, 204). In particular, polymeric body (220) of the present example includes a first outer wall (222) that extends longitudinally along the full length of an exterior surface of first spine plate (202), and an opposed second outer wall (224) that extends longitudinally along the full length of an exterior surface of second spine plate (204). Polymeric body (220) further includes an inner wall (226) that spans laterally between opposed interior surfaces of spine plates (202, 204) and extends longitudinally for the full lengths of spine plates (202, 204). As shown best in FIG. 12, polymeric body (220) further includes a bottom wall (228) that connects outer walls (222, 224) with inner wall (226) along an underside of anvil half (200). A distal end of polymeric body (220) defines a tapered distal tip (230) that connects outer walls (222, 224) with inner wall (226) at a distal end of anvil half (200). As shown best in FIGS. 6 and 10, raised medial portions (210) of spine plates (202, 204) extend above upper surfaces of outer walls (222, 224) and inner wall (226) such that medial plate portions (210) remain exposed relative to polymeric body (220). Polymeric body (220) may comprise a variety of polymeric materials, such as various plastics, and may be applied to spine plates (202, 204) and anvil plate (240) via an injection molding process, for example as described below in connection with FIGS. 26A-26B.

Figure 11:
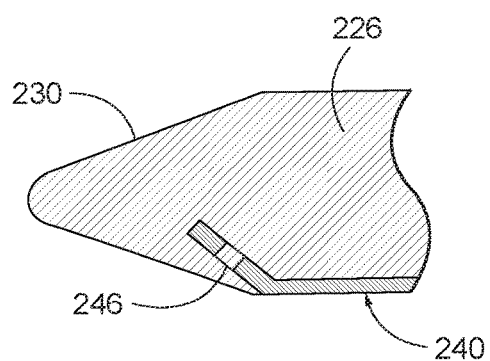
FIG. 11 depicts an enlarged side cross-sectional view of a distal end of the anvil half of FIG. 6, taken along section line 10-10 in FIG. 8.
Figure 13:
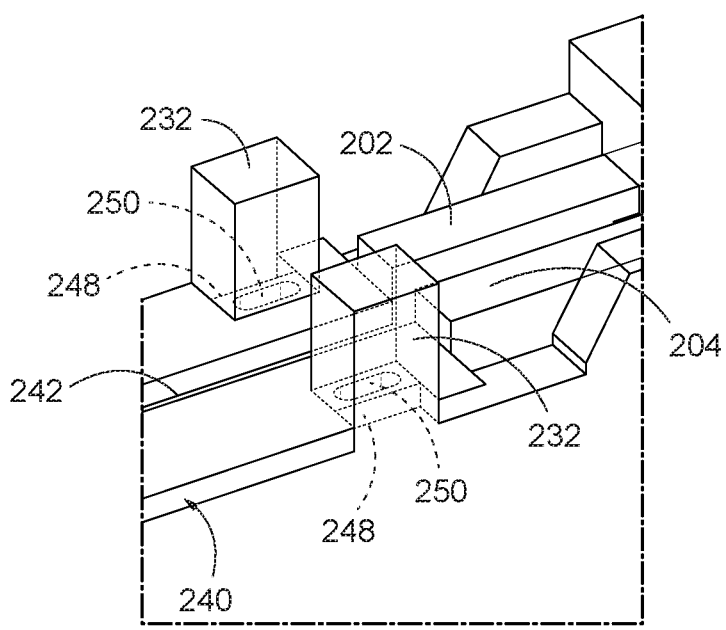
FIG. 13 depicts an enlarged perspective view of a portion of the anvil half of FIG. 6 at which a proximal end of the anvil plate is coupled with the body, showing in dashed lines certain features of the anvil plate proximal end that promote coupling of the anvil plate with the body via injection molding.

As shown in FIGS. 11-13, anvil plate (240) is secured at its proximal and distal ends to polymeric body (220). As seen in FIGS. 7 and 12, a distal portion of anvil plate (240) includes a pair of laterally spaced distal openings (244) through which corresponding portions of polymeric body (220) project. As shown in FIGS. 7 and 11, anvil plate (240) further includes an angled distal end (246) embedded within tapered distal tip (230) of polymeric body (220). In some versions of anvil half (200), distal openings (244) or angled distal end (246) may be omitted from anvil plate (240). As shown in FIGS. 12 and 13, a proximal end of anvil plate (240) includes a pair of notches (248) formed in the opposed lateral edges of anvil plate (240), and a pair of proximal openings (250) formed between notches (248) and longitudinal slot (242). As shown in FIG. 13, polymeric body (220) projects through each notch (248) and the respective proximal opening (250) to define a corresponding post (232). Posts (232) are configured to mate with a portion of a staple cartridge (not shown) when anvil half (200) is coupled with a cartridge half of a linear surgical stapler.

B. Exemplary Structural Plate Having Tapered Distal Portion

Figure 14:
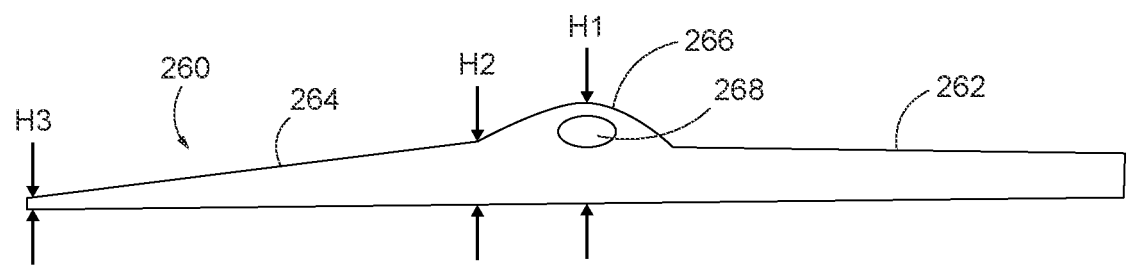
FIG. 14 depicts a side elevational view of another exemplary spine plate suitable as an alternative component of the anvil half of FIG. 6.

FIG. 14 shows an exemplary alternative spine plate (260) that may be substituted for each of spine plates (202, 204) of anvil half (200) described above. Spine plate (260) is similar to spline plates (202, 204) except as otherwise described below. Spine plate (260) includes an elongate proximal plate portion (262), an elongate distal plate portion (264), and a raised medial plate portion (266) therebetween. Like raised medial plate portions (210) of spine plates (202, 204), raised medial plate portion (266) is configured to align with and be received by a shroud, which may be similar to anvil shroud (74) described above. Raised medial portion (266) of the present version includes a finger opening (268) configured to receive one or more fingers of a user laterally therethrough to promote effective grip of the corresponding anvil half during use.

Raised medial plate portion (266) of the present version defines a maximum transverse height (H1) of spine plate (260). Distal plate portion (264) tapers uniformly in a distal direction from a second transverse height (H2) at a proximal end of distal plate portion (264) to a third transverse height (H3) at a distal end of distal plate portion (264). The second transverse height (H2) is less than the maximum transverse height (H1), and the third transverse height (H3) is less than the second transverse height (H2). In the present version, distal plate portion (264) tapers such that the third transverse height (H3) is the smallest transverse height of spine plate (260). Such a tapered configuration of distal plate portion (264) enables spine plate (260) to be formed from less material than either of spine plates (202, 204) described above, while maintaining adequate stiffness such that distal tip deflection of distal plate portion (264) under a given transverse load during clamping of tissue is no greater than the distal tip deflection of distal plate portion (208) of spine plate (202, 204) under the same transverse load.

C. Exemplary Structural Plates Having Adjoining Member

Figure 15:
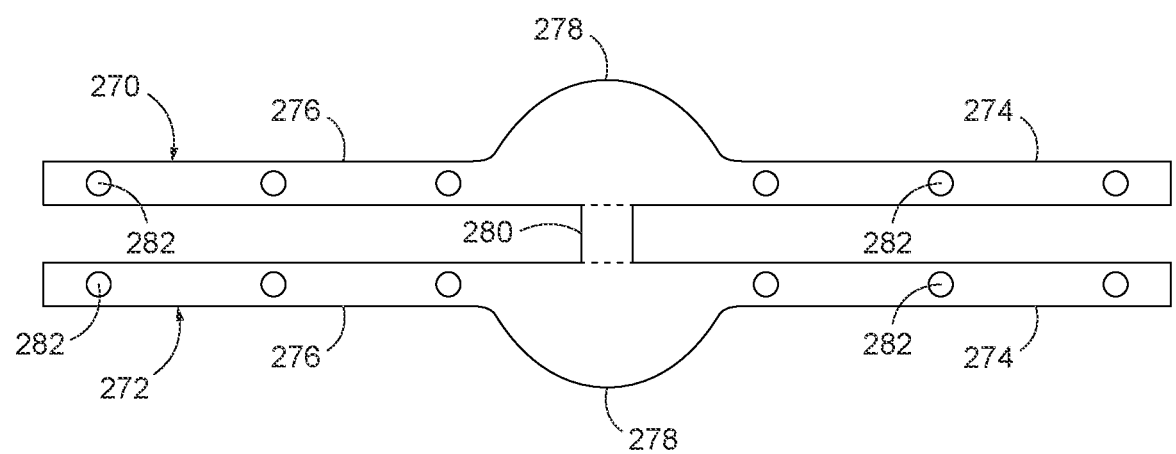
FIG. 15 depicts a top plan view of another exemplary pair of spine plates suitable as alternative components of the anvil half of FIG. 6, showing the spine plates arranged prior to being bent relative to one another about an adjoining member.

FIG. 15 shows another exemplary pair of spine plates (270, 272) that may be substituted for spine plates (202, 204) of anvil half (200) described above. Spine plates (270, 272) are similar to spine plates (202, 204) except as otherwise described below. Each spine plate (270, 272) includes an elongate proximal plate portion (274), an elongate distal plate portion (276), and a raised medial plate portion (278). Spine plates (270, 272) of the present version are integrally connected with one another by an adjoining member (280) that extends laterally from a flat side of raised medial plate portion (278) of first spine plate (270) to a flat side of raised medial plate portion (278) of second spine plate (272). In the configuration shown, spine plates (270, 272) and adjoining member (280) are arranged in a common plane such that spine plates (270, 272) and adjoining member (280) define a flat, monolithic structure. Additionally, spine plates (270, 272) are joined with respective ends of adjoining member (280) such that the raised, curved surfaces of medial plate portions (278) are opposed from one another.

During manufacturing of an anvil half containing spine plates (270, 272), each spine plate (270, 272) is bent upwardly relative to adjoining member (280) such that spine plates (270, 272) extend parallel to one another and transversely to adjoining member (280), thereby defining a structure having a U-shaped cross-section at medial plate portions (278). In the resulting structure, spine plates (270, 272) are laterally spaced from one another to receive a molded polymeric body (not shown) therebetween, yet integrally connected with one another by adjoining member (280) for enhanced rotational stiffness. Each spine plate (270, 272) of the present version further includes a plurality of openings (282) spaced longitudinally along proximal plate portion (274) and distal plate portion (276). Each opening (282) is configured to receive a respective projection of the polymeric body therethrough during the body formation process, thereby more securely anchoring spine plates (270, 272) relative to the formed polymeric body.

D. Exemplary Structural Plates Having Lateral Tab and Opening

Figure 16:
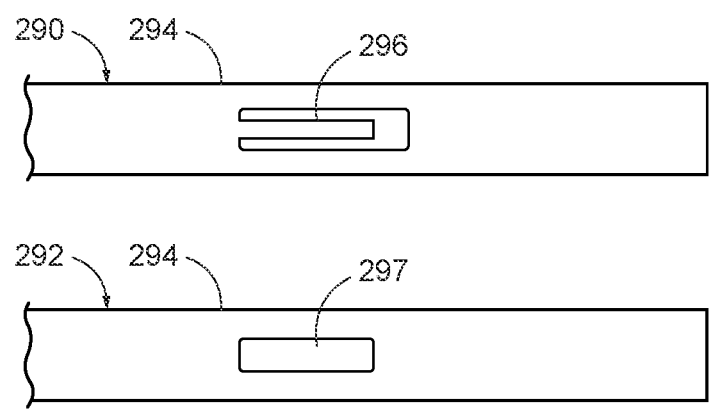
FIG. 16 depicts a top plan view of distal portions of another exemplary pair of spine plates suitable as alternative components of the anvil half of FIG. 6, showing a deformable tab formed in one spine plate and a receiving slot formed in the other spine plate.
Figure 17:
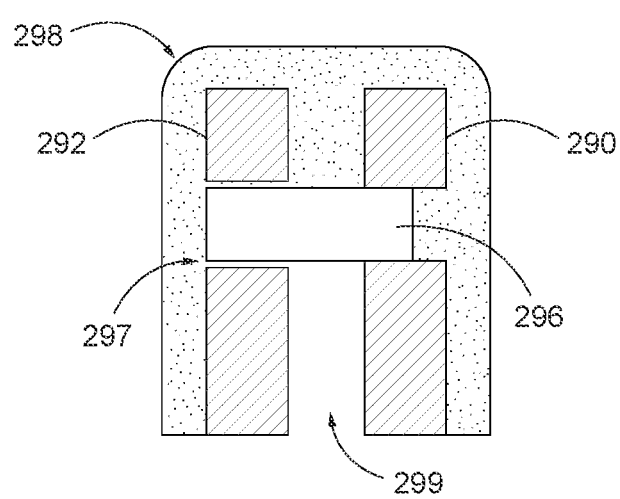
FIG. 17 depicts an end cross-sectional view of the spine plates of FIG. 16, showing the spine plates arranged such that the spine plates confront one another and such that the deformable tab is received by the receiving slot, additionally showing a body formed about the spine plates.

FIGS. 16-17 show portions of another exemplary pair of spine plates (290, 292), which may be similar to spine plates (202, 204) of anvil half (200) described above except as otherwise described below. In particular, an elongate distal plate portion (294) of first spine plate (290) includes a projection in the form of an elongate bendable tab (296), and an elongate distal plate portion (294) of second spine plate (292) includes an opening in the form of a longitudinal slot (297). During manufacturing of a corresponding anvil half, spine plates (290, 292) are positioned parallel to one another and bendable tab (296) of first spine plate (290) is bent toward second spine plate (292) such that a free end of bent tab (296) is received by slot (297), as shown in FIG. 17. This establishes a direct mechanical coupling between spine plates (290, 292) that enhances rotational stiffness of the resulting anvil half once a polymeric body (298) is formed to at least partially encapsulate spine plates (290, 292). In the present example, tab (296) and slot (297) are spaced transversely away from surfaces of spine plates (290, 292) and polymeric body (298) to accommodate a longitudinal slot (299) configured to slidably receive a portion of a knife member (not shown) therethrough during firing of a linear surgical stapler. It will be appreciated that spine plate coupling features similar to adjoining member (280) and/or tab (296) and slot (297) may be incorporated into any of the exemplary configurations disclosed herein.

Figure 18:
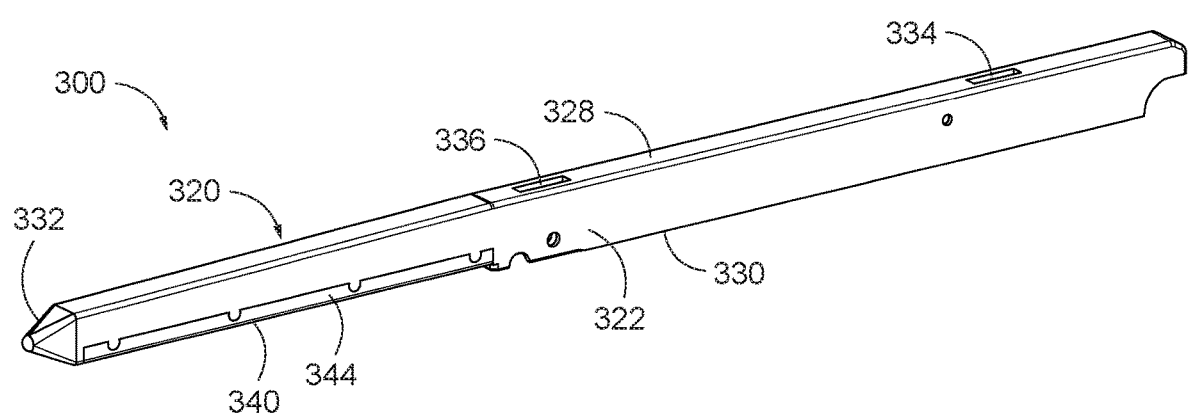
FIG. 18 depicts a perspective view of another exemplary anvil half of a linear surgical stapler, having a pair of spine plates, an anvil plate, and a body.

E. Exemplary Anvil Half Having Structural Plates with Proximal Portions Fully Encapsulated by Molded Body FIG. 18 shows another exemplary anvil half (300) of a linear surgical stapler that is similar to anvil half (200) described above except as otherwise described below. Anvil half (300) includes a pair of elongate inner structural members in the form spine plates (302, 304) (see FIG. 19), a polymeric body (320) molded about spine plates (302, 304), and an anvil plate (340) coupled with distal portions of polymeric body (320) and spine plates (302, 304). As described in greater detail below, proximal plate portions (306) of spine plates (302, 304) are fully encapsulated by polymeric body (320).

Figure 19:
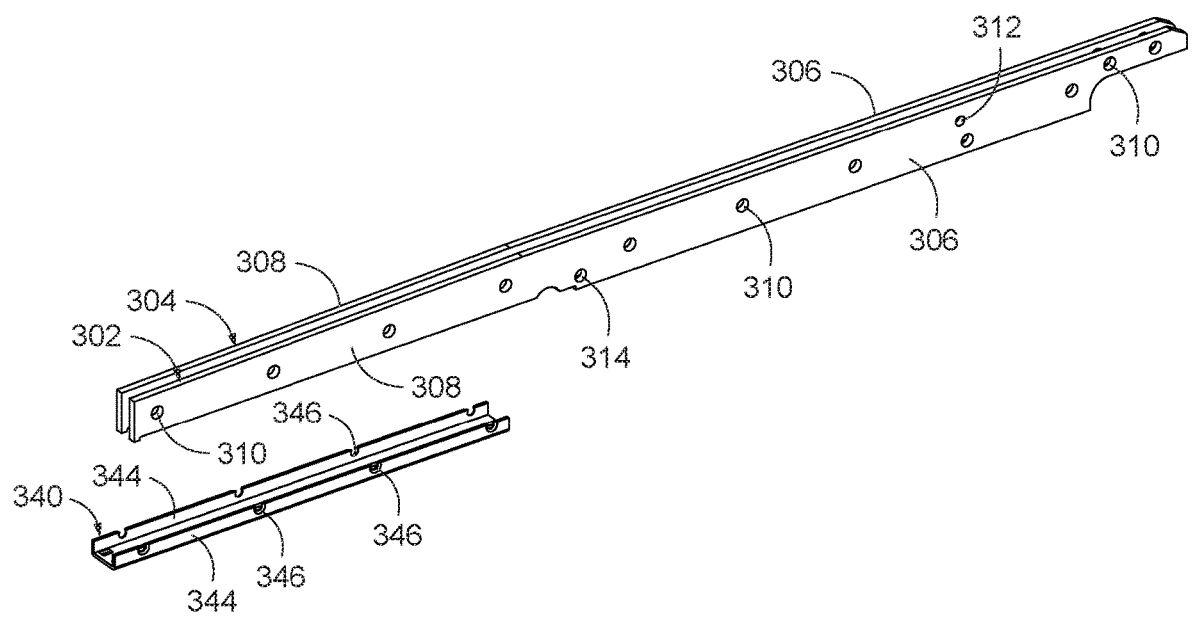
FIG. 19 depicts a perspective view of the spine plates and the anvil plate of the anvil half of FIG. 18, showing the anvil plate separated from the spine plates before the body is formed about the spine plates and the anvil plate.

As shown best in FIG. 19, spine plates (302, 304) of the present example are spaced laterally from one another and are arranged parallel to and equidistantly from a longitudinal axis of anvil half (300), and transversely to a tissue clamping plane defined by anvil plate (340). Each spine plate (302, 304) includes an elongate proximal plate portion (306) and an elongate distal plate portion (308) extending directly from proximal plate portion (306). Each spine plate (302, 304) further includes a plurality of lateral openings (310) spaced along a length thereof. Each opening (310) is configured to receive a respective projection of polymeric body (320) therethrough during the formation of polymeric body (320) to provide a secure connection between body (320) and each spine plate (302, 304). In some versions, a proximally located pair of openings (312) is configured to receive a first pin (not shown) laterally therethrough, and a medially located pair of openings (314) is configured to receive a second pin (not shown) laterally therethrough. Such pins may be configured to be releasably captured by corresponding portions of a cartridge half of a linear surgical stapler, for example in the manner disclosed in U.S. application Ser. No. 16/102,164, issued as U.S. Pat. No. 10,898,187 on Jan. 26, 2021 and U.S. application Ser. No. 16/102,170, published as U.S. Pub. No. 2020/0046353 on Feb. 13, 2020, incorporated by reference above. In other versions, the structure otherwise provided by such pins may be defined by polymeric body (320) extending laterally through openings (312, 314).

Figure 20:
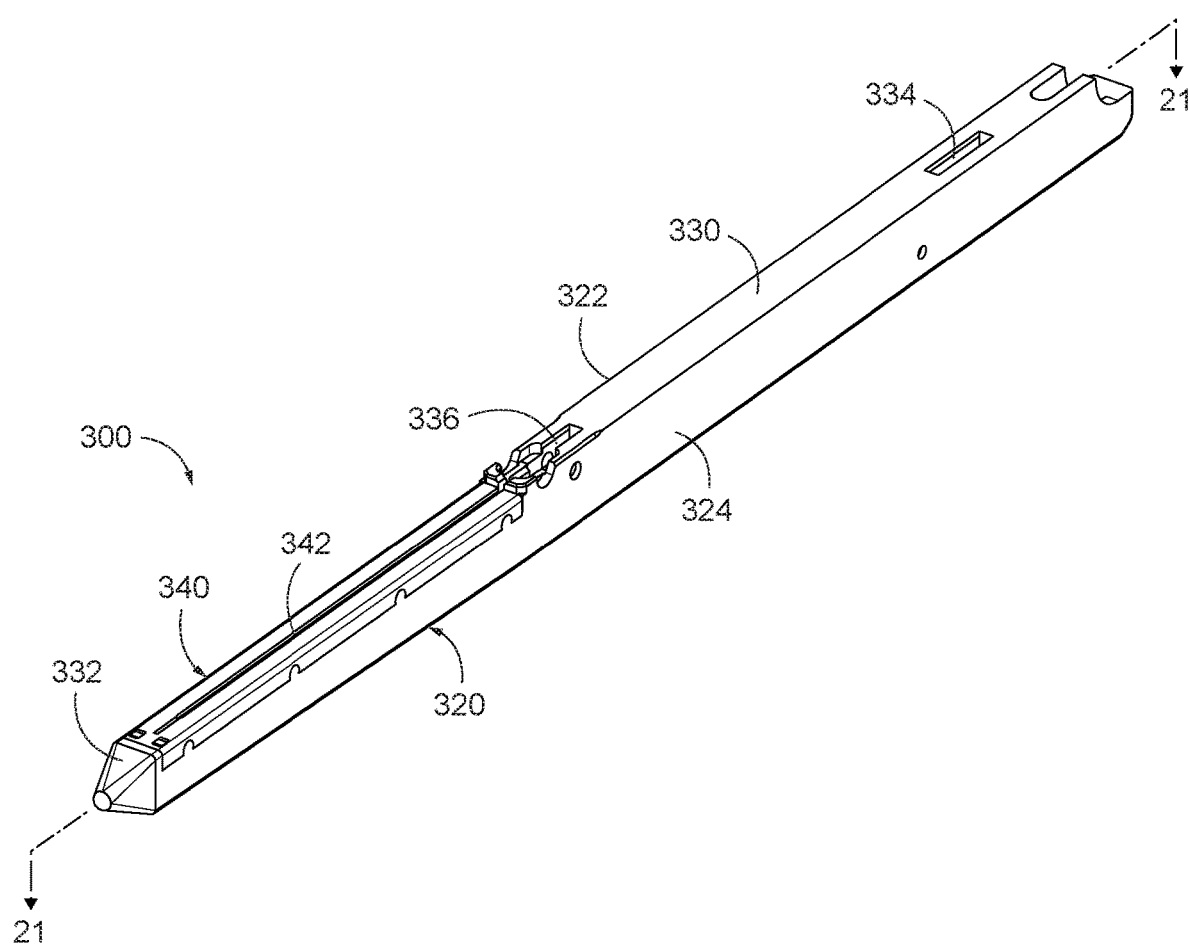
FIG. 20 depicts another perspective view of the anvil half of FIG. 18, showing the anvil half oriented such that the anvil plate faces upwardly.

Anvil plate (340) is similar to anvil plate (240) described above in that anvil plate (340) includes a longitudinal slot (342), shown in FIG. 20, configured to slidably receive a knife member (not shown) therethrough. Though not shown, anvil plate (340) further includes a plurality of staple-forming pockets, which may be similar to pockets (906a, 906b) of anvil plate (900) described below. As shown in FIGS. 19 and 20, anvil plate (340) is oriented transversely to spine plates (302, 304) such that anvil plate (340) is supported by and spans laterally across lower edges of elongate distal plate portions (308) of spine plates (302, 304). Anvil plate (340) of the present example further includes a pair of sidewalls 044) each configured to overlap a portion of an exterior side surface of a respective spine plate (302, 304). Each sidewall (344) includes a plurality of lateral openings (346) that are spaced longitudinally along and open to a free edge of the sidewall (344). Each opening (346) is configured to receive a respective portion of polymeric body (320) therein during formation of body (320) to provide secure attachment of anvil plate (340) to polymeric body (320).

Figure 21:
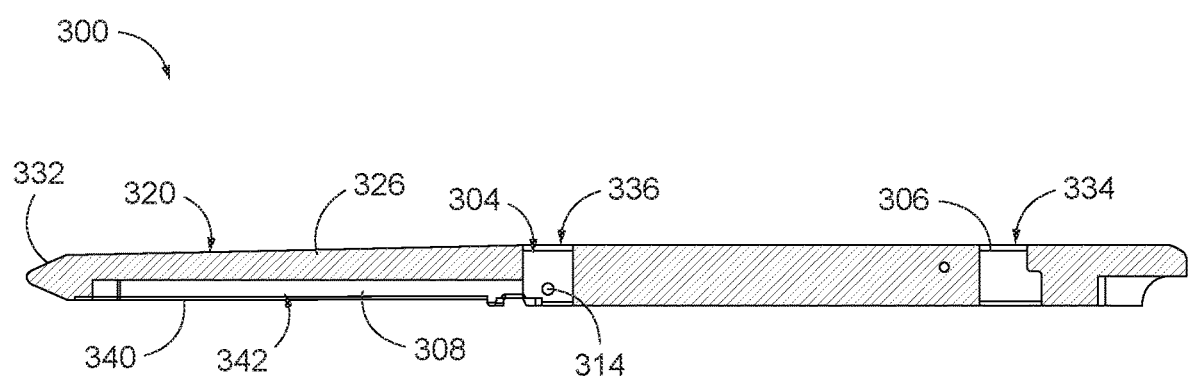
FIG. 21 depicts a side cross-sectional view of the anvil half of FIG. 18, taken along section line 21-21 in FIG. 20.

As shown best in FIGS. 18, 20, and 21, polymeric body (320) is formed about spine plates (302, 304) such that at least a proximal portion of polymeric body (320) fully encapsulates each spine plate (302, 304). Polymeric body (320) of the present example includes a first outer wall (322) that extends longitudinally along the full length of an exterior surface of first spine plate (302), and an opposed second outer wall (324) that extends longitudinally along the full length of an exterior surface of second spine plate (304).

Polymeric body (320) further includes an inner wall (326) that spans laterally between opposed interior surfaces of spine plates (302, 304), and which extends longitudinally for a full length of spine plates (302, 304). As shown best in FIG. 18, polymeric body (320) further includes a top wall (328) that extends longitudinally for a full length of spine plates (302, 304) and interconnects with outer walls (322, 324) and inner wall (326). As shown best in FIG. 20, polymeric body (320) further includes a bottom wall (330) that extends longitudinally along the bottom edges of proximal plate portions (306) and interconnects with outer walls (322, 324) and inner wall (326).

Outer walls (322, 324), inner wall (326), top wall (328), and bottom wall (330) of polymeric body (320) join together at the proximal ends of spine plates (302, 304) to define a portion of body (320) that extends proximally beyond the proximal ends of spine plates (302, 304). Accordingly, as shown throughout FIGS. 18-21, polymeric body (320) fully encapsulates proximal plate portions (306) of spine plates (302, 304). Additionally, outer walls (322, 324) and inner wall (326) of polymeric body (320) join together at the distal ends of spine plates (302, 304) to define a tapered distal tip (332) that extends distally beyond the distal ends of spine plates (302, 304). Accordingly, polymeric body (320) cooperates with anvil plate (340) to fully encapsulate distal plate portions (308) of spine plates (302, 304).

As shown in FIGS. 18, 20, and 21, polymeric body (320) of the present example further includes a proximally located slot (334) and a medially located slot (336) spaced longitudinally from one another. Each slot (334, 336) extends transversely though top wall (328), inner wall (326), and bottom wall (330). Slots (334, 336) may be configured to facilitate mating of polymeric body (320) with a shroud (not shown), which may be similar to anvil shroud (74) described above. Similar to polymeric body (220) of anvil half (200) described above, polymeric body (320) may comprise any suitable polymeric material and may be formed about spine plates (302, 304) and anvil plate (340) via an injection molding process, such as the exemplary process described below in connection with FIGS. 26A-26B.

F. Exemplary Anvil Half Having Molded Body with Integrated Shroud

Figure 22:
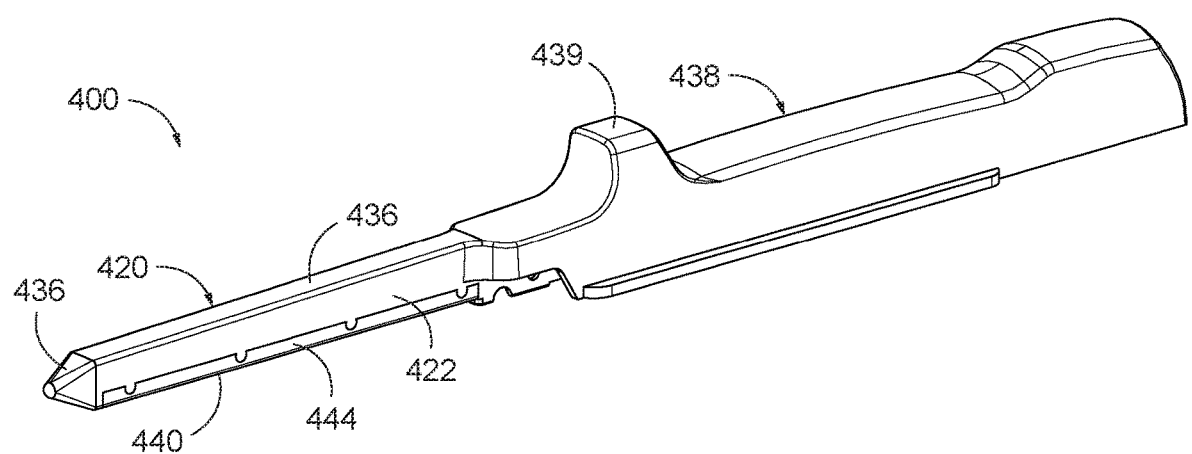
FIG. 22 depicts a perspective view of another exemplary anvil half of a linear surgical stapler, having a pair of spine plates, an anvil plate, and a body having an integrated shroud portion.

FIG. 22 shows another exemplary anvil half (400) of a linear surgical stapler that is similar to anvil halves (200, 300) described above except as otherwise described below. Anvil half (400) includes a pair of elongate inner structural members in the form spine plates (402, 404), a polymeric body (420) molded about spine plates (402, 404), and an anvil plate (440) coupled with distal portions of polymeric body (420) and spine plates (402, 404). As described in greater detail below, polymeric body (420) of the present example includes an integrated shroud portion (438) that is formed simultaneously with the other portions of polymeric body (420).

Figure 23:
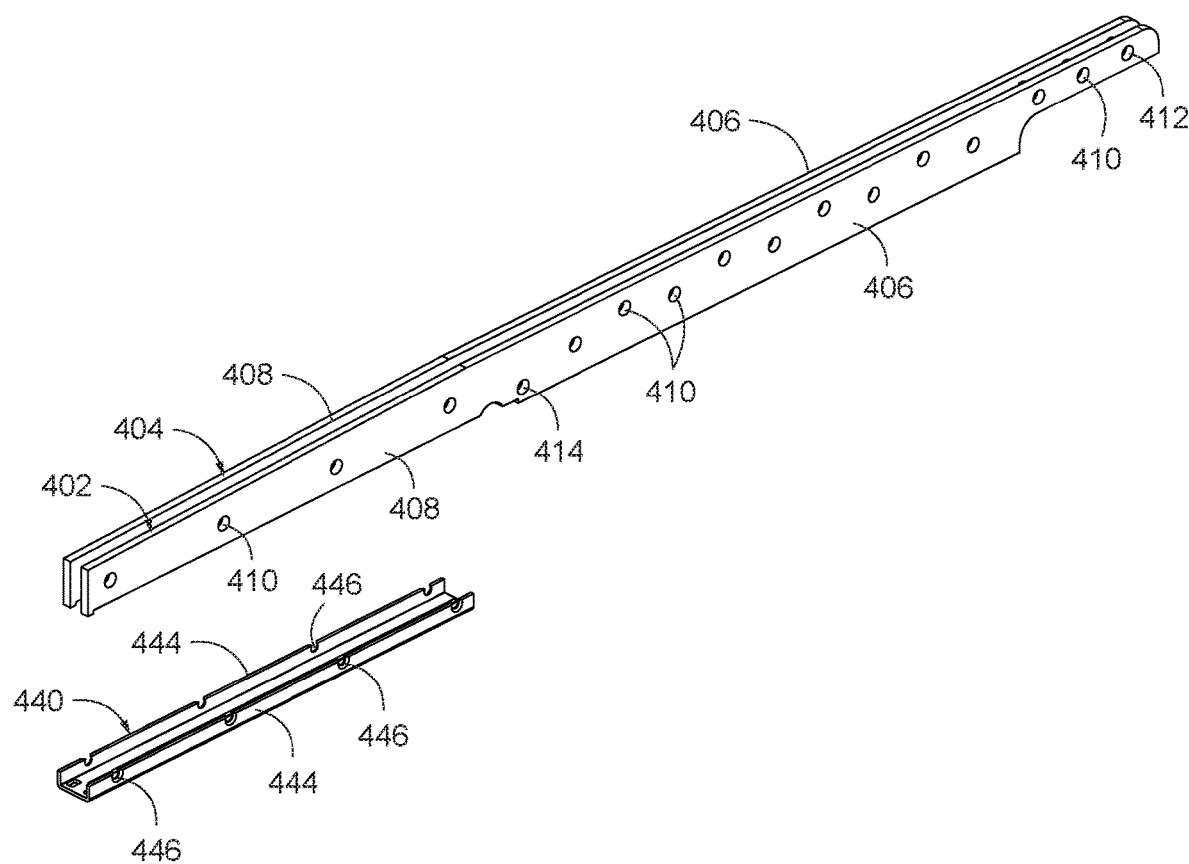
FIG. 23 depicts a perspective view of the spine plates and the anvil plate of the anvil half of FIG. 22, showing the anvil plate separated from the spine plates before the body is formed about the spine plates and the anvil plate.

Spine plates (402, 404) of the present example are substantially similar to spine plates (302, 304) of anvil half (300) described above, except as otherwise described below. As shown in FIG. 23, spine plates (402, 404) are spaced laterally from one another and are arranged parallel to and equidistantly from a longitudinal axis of anvil half (400), and transversely to a tissue clamping plane defined by anvil plate (440). Each spine plate (402, 404) includes an elongate proximal plate portion (406) and an elongate distal plate portion (408) extending directly from proximal plate portion (406). Each spine plate (402, 404) further includes a plurality of lateral openings (410) spaced along a length thereof. Each opening (410) is configured to receive a respective projection of polymeric body (420) laterally therethrough during the formation of polymeric body (420) to provide a secure connection between body (420) and each spine plate (402, 404). In some versions, a proximally located pair of openings (412) may be configured to receive a first pin (not shown) laterally therethrough, and a medially located pair of openings (414) may be configured to receive a second pin (not shown) laterally therethrough. Such pins may be configured to be releasably captured by corresponding portions of a cartridge half of a linear surgical stapler, for example in the manner disclosed in U.S. application Ser. No. 16/102,164 issued as U.S. Pat. No. 10,898,187 on Jan. 26, 2021 and U.S. application Ser. No. 16/102,170, published as U.S. Pub. No. 2002/0046353 on Feb. 13, 2020, incorporated by reference above. In other versions, the structure otherwise provided by such pins may be defined by polymeric body (420).

Anvil plate (440) is substantially similar to anvil plate (340) described above. Anvil plate (440) includes a longitudinal slot (442), shown in FIG. 24, configured to slidably receive a knife member (not shown) therethrough. Though not shown, anvil plate (440) further includes a plurality of staple-forming pockets, which may be similar to pockets (906a, 906b) of anvil plate (900) described below. As shown best in FIGS. 23 and 24, anvil plate (440) is oriented transversely to spine plates (402, 404) such that anvil plate (440) is supported by and spans laterally across lower edges of elongate distal plate portions (408). Similar to anvil plate (340), anvil plate (440) further includes a pair of sidewalls (444) each configured to overlap a portion of an exterior side surface of a respective spine plate (402, 404). Each sidewall (444) includes a plurality of lateral openings (446) that are spaced longitudinally along and open to a free edge of the sidewall (444). Each opening (446) is configured to receive a respective portion of polymeric body (420) therein during formation of body (420) to provide secure attachment of anvil plate (440) to polymeric body (420).

Figure 24:
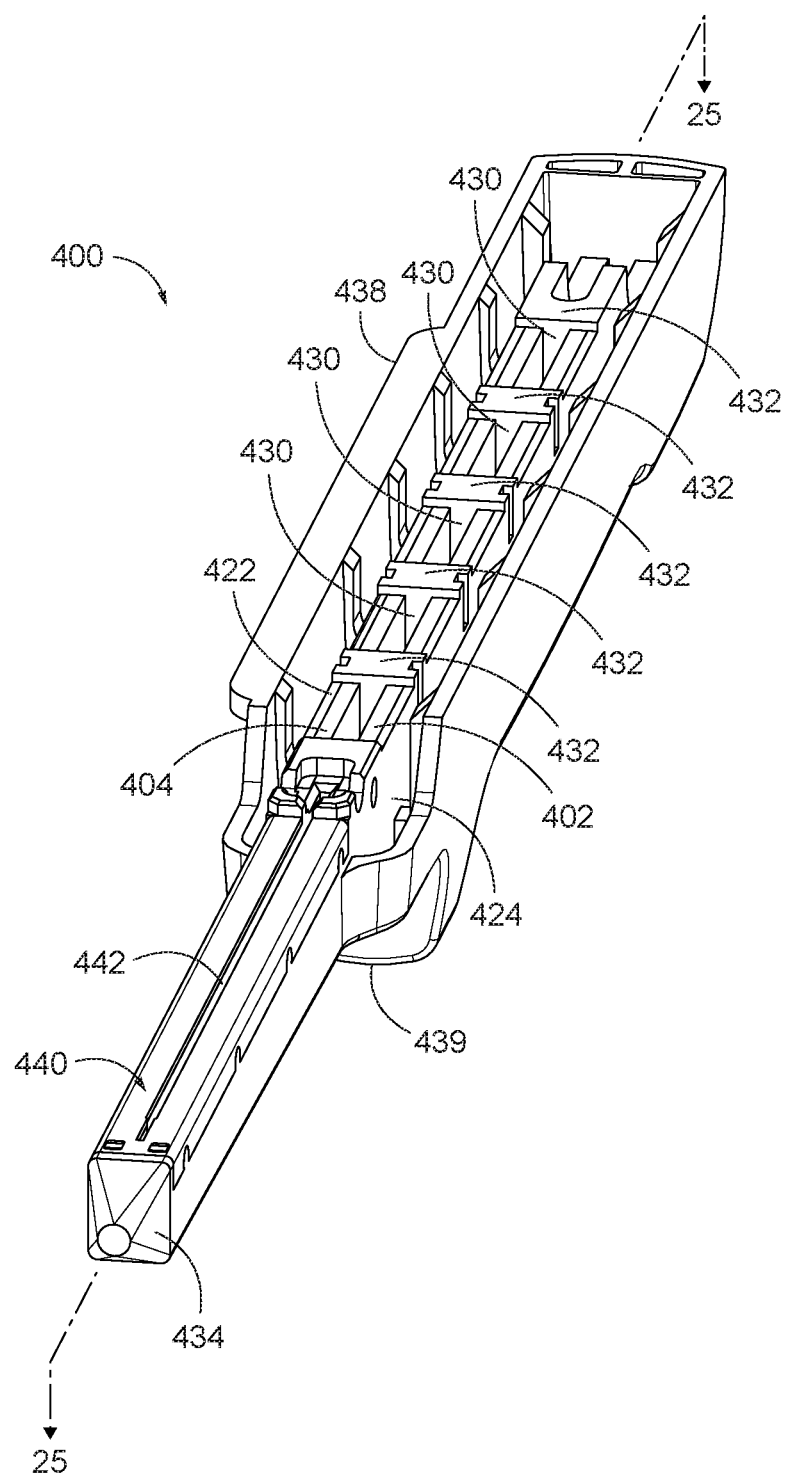
FIG. 24 depicts another perspective view of the anvil half of FIG. 22, showing the anvil half oriented such that the anvil plate faces upwardly.
Figure 25:
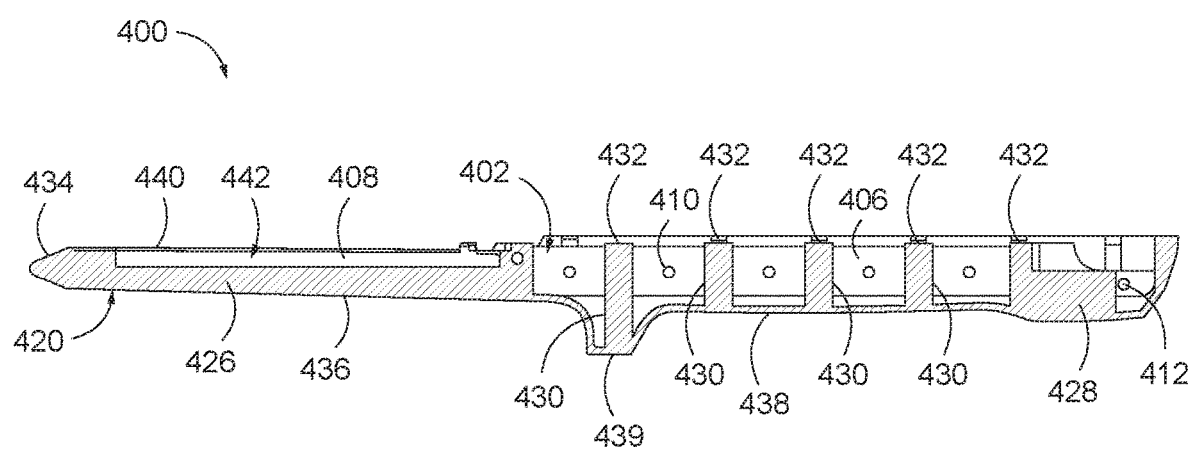
FIG. 25 depicts a side cross-sectional view of the anvil half of FIG. 22, taken along section line 25-25 in FIG. 24.

As shown best in FIGS. 24 and 25, polymeric body (420) is formed about spine plates (402, 404) such that polymeric body (420) encapsulates at least a portion of each spine plate (402, 404). In particular, polymeric body (420) of the present example includes a first outer wall (422) that extends longitudinally along the full length of an exterior surface of first spine plate (402), and an opposed second outer wall (424) that extends longitudinally along the full length of an exterior surface of second spine plate (404). Polymeric body (420) further includes an inner wall having multiple portions (426, 428, 430) that span laterally between opposed interior surfaces of spine plates (402, 404). In particular, the inner wall includes a distal inner wall portion (426) that extends longitudinally between distal plate portions (408), a proximal inner wall portion (428) that extends between the proximal ends of proximal plate portions (406), and a plurality of inner wall segments (430) spaced longitudinally along proximal plate portions (406) between distal inner wall portion (426) and proximal inner wall portion (428). As shown best in FIG. 24, polymeric body (420) further includes a plurality of bottom wall segments (432) spaced longitudinally along proximal plate portions (406) and which extend laterally to connect inner wall segments (430) with lower sides of first and second outer walls (422, 424). Polymeric body (420) further defines a tapered distal tip (434) that joins first outer wall (422), second outer wall (424), and distal inner wall portion (426) at their distal ends. As shown best in FIGS. 22 and 25, a top wall (436) of polymeric body (420) extends longitudinally along the upper edges of distal plate portions (408) and joins with distal portions of outer walls (422, 424), with distal inner wall portion (426), and with tapered distal tip (434).

Polymeric body (420) of the present example further includes an integrated shroud portion (438) that is generally similar in shape to anvil shroud (74) described above and which is formed integrally with the remaining portions of polymeric body (420). As shown in FIG. 24, integrated shroud portion (438) is arranged outwardly of and extends longitudinally alongside first and second outer walls (422, 424). As shown best in FIGS. 24 and 25, integrated shroud portion (438) joins at its proximal end with outer walls (422, 424) and proximal inner wall portion (428). As shown best in FIGS. 22 and 25, integrated shroud portion (438) joins at its distal end with outer walls (422, 424), distal inner wall portion (426), and top wall (436). As shown in FIG. 25, integrated shroud portion (438) joins with inner wall segments (430) along the length of integrated shroud portion (438). In this manner, integrated shroud portion (438) covers the top edges of proximal plate portions (406) of spine plates (402, 404), and wraps circumferentially around outer walls (422, 424) toward a bottom side of anvil half (400). Integrated shroud portion (438) is suitably shaped to provide gripping features for a user, including an outwardly projecting distal shoulder (439), and thus eliminates the need for a separate shroud structure. Similar to polymeric bodies (220, 320) of anvil halves (200, 300), polymeric body (420) may comprise any suitable polymeric material and may be formed about spine plates (402, 404) and anvil plate (440) via an injection molding process, such as the exemplary process described below in connection with FIGS. 26A-26B.

Figure 26A:
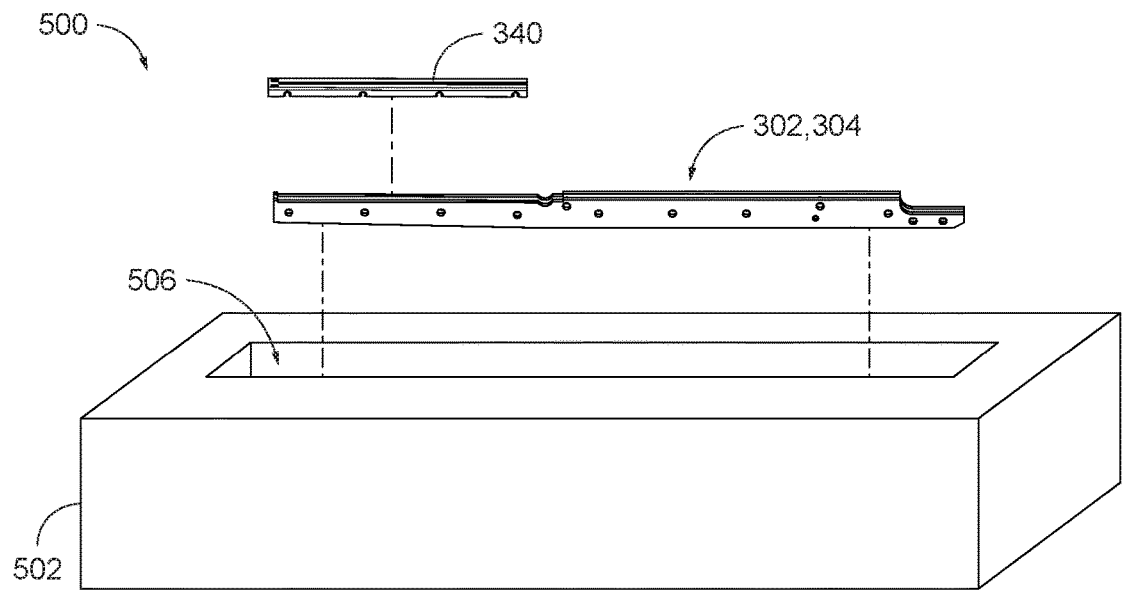
FIG. 26A depicts a schematic perspective view of the spine plates and the anvil plate of FIG. 19, and a bottom mold plate of an exemplary injection molding system, showing the spine plates and anvil plate being positioned within a mold cavity of the bottom mold plate.
Figure 26B:
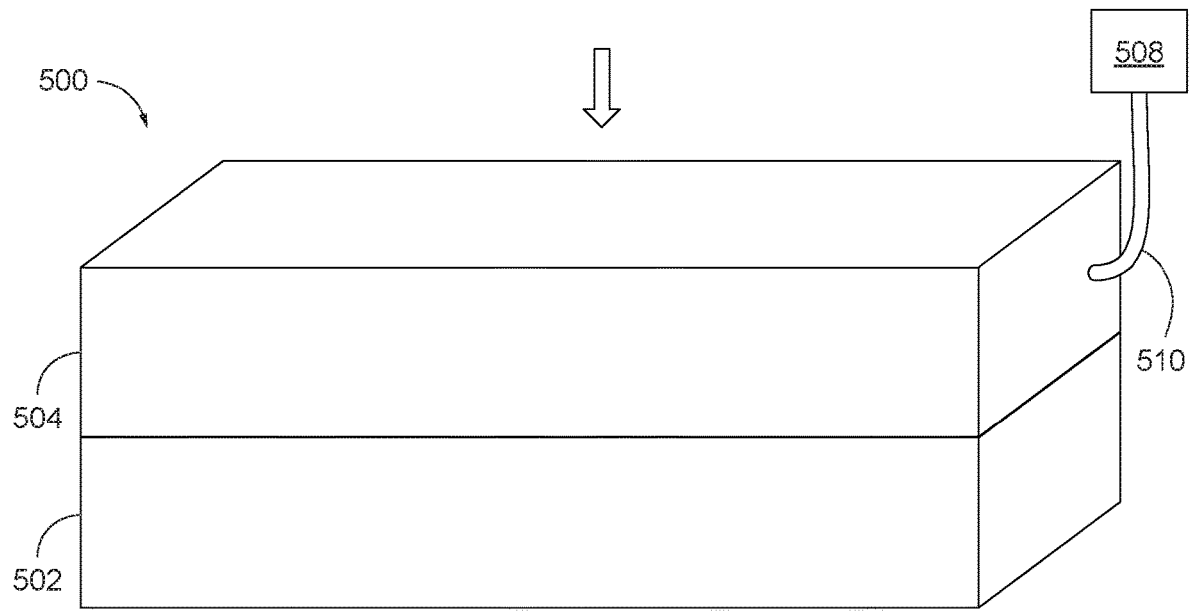
FIG. 26B depicts a schematic perspective view of the injection molding system of FIG. 26A, showing an upper mold plate lowered onto the bottom mold plate and a polymeric material being injected into the mold cavity to form a polymeric body about the spine plates and anvil plate to create the anvil half of FIG. 18.

G. Exemplary Process for Making Stapler Half with Structural Plates and Molded Body FIGS. 26A-26B show an exemplary process for forming a polymeric body of a portion of a linear surgical stapler, such as an anvil half, using an injection molding system (500). The process and system (500) are illustrated in combination with spline plates (302, 304) and anvil plate (340) for forming polymeric body (320) of anvil half (300), described above in connection with FIG. 18. However, it will be appreciated that the process and system (500) may also be implemented for forming any of the other exemplary anvil halves (200, 400) described above. Injection molding system (500), shown schematically, generally includes a first mold half (502), a second mold half (504), a mold cavity (506) defined between mold halves (502, 504), and a material supply (508), among various other components not shown that will be readily apparent to those of ordinary skill in the art of injection molding. Material supply (508) is configured to house a polymeric material, such as a plastic, and is further configured to direct the polymeric material in liquid form to mold cavity (506) via a feed line (510), as described below.

FIG. 26A shows a first stage of the exemplary formation process in which spine plates (302, 304) are positioned within mold cavity (506) such that spine plates (302, 304) extend parallel to one another and are spaced laterally from one another. Anvil plate (340) is positioned relative to spine plates (302, 304) such that anvil plate (340) extends laterally across distal plate portions (308), and transversely to spine plates (302, 304). While spine plates (302, 304) and anvil plate (340) are shown oriented such that anvil plate (340) is positioned on top and spine plates (302, 304) are positioned underneath, it will be understood that plates (302, 304, 340) may be provided in other orientations in other examples. In some versions, staple-forming pockets similar to pockets (906a, 906b) described below may be formed in anvil plate (340) before the injection molding process, and in other versions such staple-forming pockets in anvil plate (340) may be formed after the injection molding process.

Once spine plates (302, 304) and anvil plate (340) are suitably positioned within mold cavity (506), mold halves (502, 504) are brought together as seen in FIG. 26B. Liquid polymeric material is then directed from material supply (508), through feed line (510), and into mold cavity (506). The injected polymeric material encapsulates and forms around select portions of spine plates (302, 304) and anvil plate (340) to define the various portions of polymeric body (320) described above. The injected polymeric material is allowed to cure within mold cavity (506), and mold halves (502, 504) are then separated to reveal anvil half (300) in which polymeric body (320) is overmolded onto spine plates (302, 304) and is coupled with anvil plate (340) in the manner described above. Though not shown, various additional finishing steps apparent to those of ordinary skill in the art may be performed on polymeric body (320) before anvil half (300) is combined with a suitable cartridge half to define a complete linear surgical stapler ready for surgical use.

III. Exemplary Firing Assembly Having Separable Knife Pusher and Knife Member with Integrated Driver Ramps As described above in connection with FIGS. 2-3, cartridge half (12) of linear surgical stapler (10) utilizes a firing assembly (34) that comprises a sled (100) having integrated ramps (106), and a knife member (104) fixedly coupled to sled (100). Sled (100), including knife member (104) and ramps (106), is housed within staple cartridge (80) and is configured to couple with the distal end of an elongate actuating beam (or "knife pusher") of cartridge half (12) when staple cartridge (80) is installed within distal frame portion (20) of cartridge channel (16). Accordingly, each time a new staple cartridge (80) is installed, an entirely new sled (100) and knife member (104) is also provided. In some instances, manufacturing costs may be reduced by providing an alternative configuration of firing assembly (34) that eliminates the need to provide each staple cartridge (80) with its own sled (100) having a full set of ramps (106), while still providing each staple cartridge (80) with its own knife member.

FIGS. 27-30 show an exemplary firing assembly (600) suitable for use with a linear surgical stapler, such as stapler (10) described above or any of the exemplary staplers disclosed in the references incorporated by reference herein, such as U.S. application Ser. No. 16/102,164 issued as U.S. Pat. no. 10,898,187 on Jan. 26, 2021 or U.S. application Ser. No. 16/102,170, published as U.S. Pub. No. 2020/0046353 on Feb. 13, 2020. Firing assembly (600) includes an elongate actuating beam (602) (or "knife pusher") and a firing member (612) configured to releasably couple with a distal end (606) of actuating beam (602). Actuating beam (602) is configured to be slidably retained within a cartridge channel (not shown) of a linear surgical stapler, such as cartridge channel (16) of stapler (10) describe above. Firing member (612) is configured to be housed within a staple cartridge (not shown), which may be similar to staple cartridge (80) described above.

Actuating beam (602) of the present example includes a proximal end (604) configured to operatively couple with a firing knob (not shown) of a surgical stapler, such as firing knob (38) of stapler (10) described above. Distal end (606) of actuating beam (602) includes an upwardly extending tab (608) and an integrated first ramp (610) that extends distally from upwardly extending tab (608) and is laterally offset from a first lateral side of actuating beam (602). As shown best in FIGS. 29 and 30, firing member (612) includes a central body (614), a distally swept knife (616) projecting upwardly from central body (614), and an integrated second ramp (618) laterally offset from a second lateral side of central body (614). A proximal end of firing member (612) includes a downwardly extending tab (620) configured to mate with upwardly extending tab (608) of actuating beam (602) when a staple cartridge (not shown) housing firing member (612) is coupled to a stapler cartridge half (not shown) containing actuating beam (602).

Figure 27:
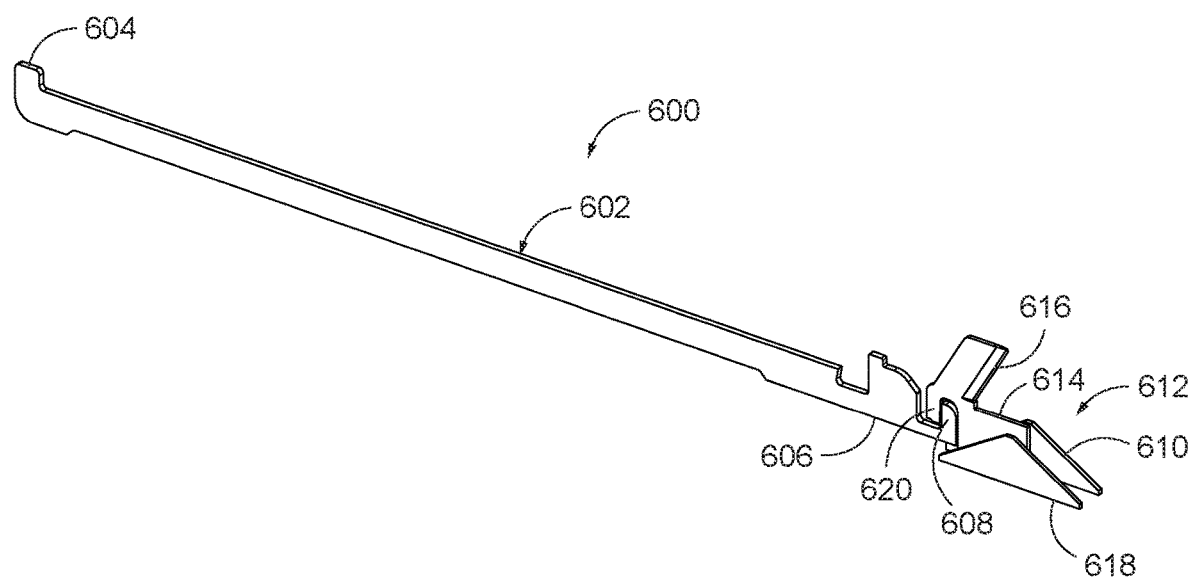
FIG. 27 depicts a perspective view of an exemplary firing assembly having a knife pusher, a firing member coupled to the knife pusher, a first ramp formed integrally with the knife pusher, and a second ramp formed integrally with the firing member.
Figure 28:
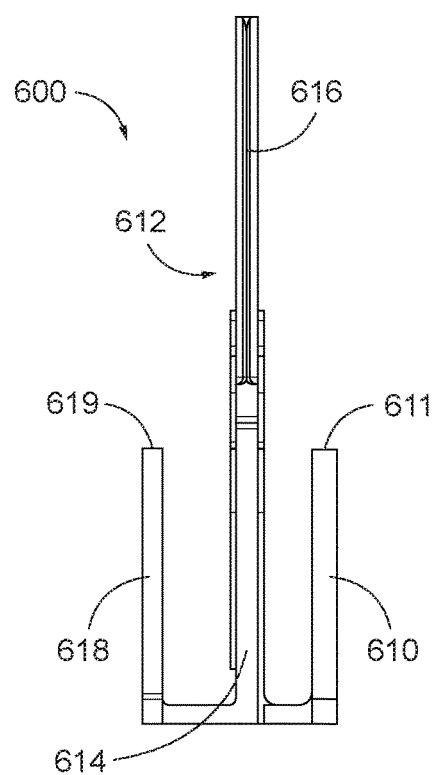
FIG. 28 depicts a distal end elevational view of the firing assembly of FIG. 27, showing the firing member coupled with the knife pusher.
Figure 29:
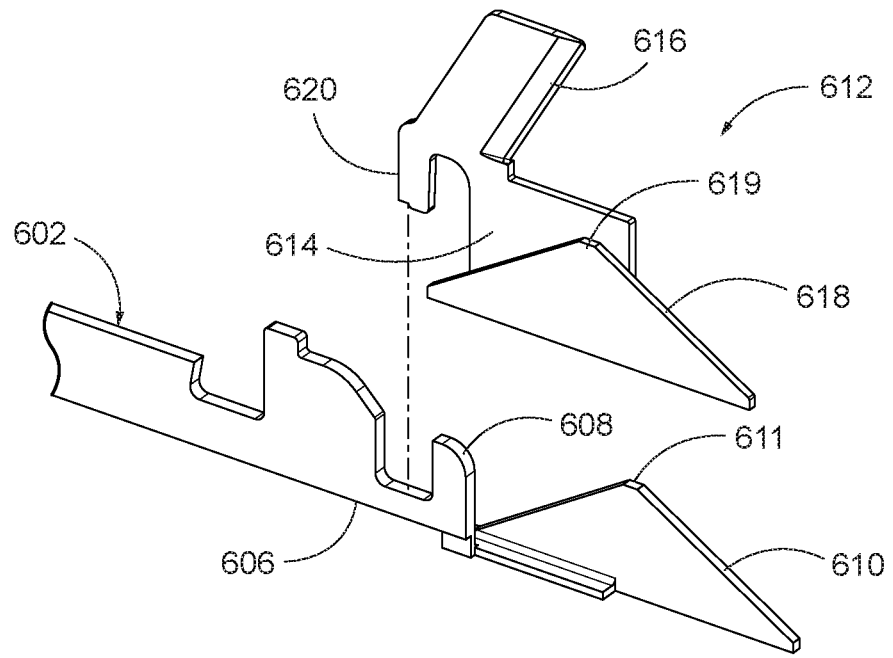
FIG. 29 depicts a disassembled perspective view of the distal end of the firing assembly of FIG. 27, showing the firing member separated from the knife pusher.
Figure 30:
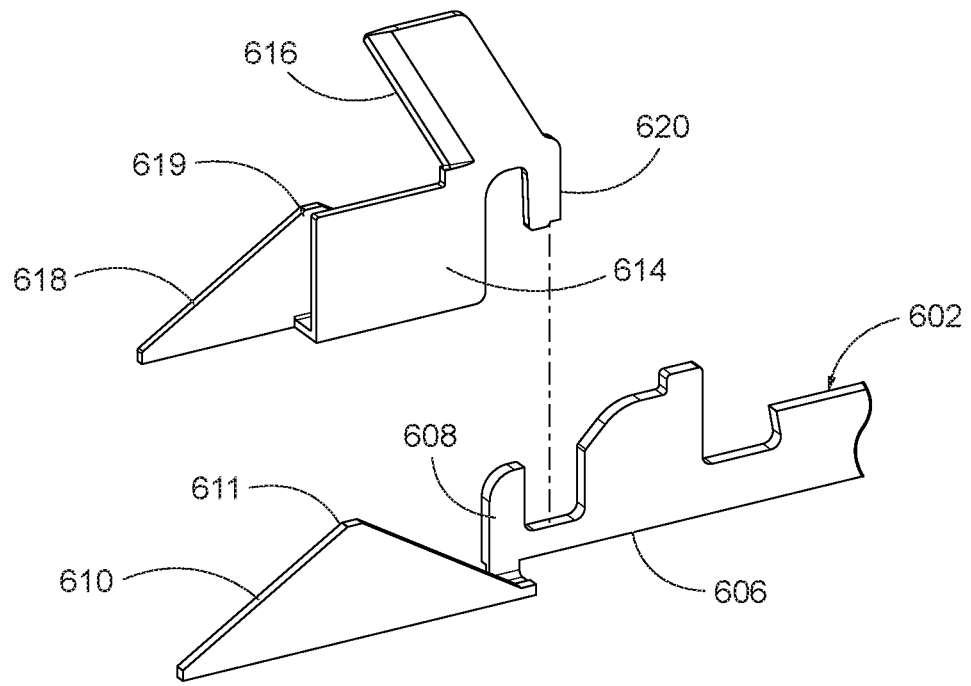
FIG. 30 depicts another disassembled perspective view of the distal end of the firing assembly of FIG. 27, showing the firing member separated from the knife pusher.

As shown in FIGS. 27 and 28, actuating beam (602) and firing member (612) mate together such that first ramp (610) extends along and is laterally offset from a first lateral side of firing assembly (600), and such that second ramp (618) extends along and is laterally offset from a second lateral side of firing assembly (600). Ramps (610, 618) are functionally similar to ramps (610, 618) of sled (100) described above in that ramps (610, 618) are configured to actuate staple drivers (86) of a staple cartridge (80) upwardly to thereby fire staples (88) into tissue while knife (616) simultaneously cuts the tissue, in response to distal advancement of firing assembly (600).

Advantageously, the configurations of actuating beam (602) and firing member (612) described above provides for simplified manufacturing by enabling each component (602, 612) to be formed from a respective blank of sheet metal without complex machining or injection molding steps. In particular, actuating beam (602) may be initially formed as a first blank in which an upper apex (611) of first ramp (610) points away from an upper side of actuating beam (602). Similarly, firing member (612) may be initially formed as a second blank in which an upper apex (619) of second ramp (618) points away from knife (616). Subsequently, the first blank may be bent such that upper apex (611) of first ramp (610) is pointed toward the upper side of actuating beam (602), and the second blank may be bent such that upper apex (619) of second ramp (618) is pointed toward knife (616), to yield the final shapes shown in FIGS. 27-30. This simplified method of manufacture reduces part quantity and minimizes manufacturing costs while still providing a configuration of firing assembly (600) that enables an independent, fresh knife (616) to be provided in each staple cartridge.

IV. Exemplary Clamp Lever Blocking Features

As described above in connection with linear surgical stapler (10), anvil half (14) is assembled with cartridge half (12) such that latch projections (56) of anvil half (14) are received within vertical slots defined by side flanges (22) of cartridge channel (16). Clamp lever (24) is then pivoted from an open position to a closed position to capture latch projections (56) and thereby clamp anvil half (14) against cartridge half (12). As shown in FIG. 4A, clamp lever (24) must be maintained in the open position for latch projections (56) to be properly received by the vertical slots of cartridge channel (16) and jaws (30) of clamp lever (24).

In some instances, it may be desirable to provide a linear surgical stapler with features that ensure the clamp lever is maintained in an open position and does not rotate closed until the stapler halves are sufficiently approximated such that the latch projections of the anvil half are positioned to be captured by features of the cartridge half. The exemplary linear surgical staplers (700, 800) described below include exemplary versions of such features.

Figure 31:
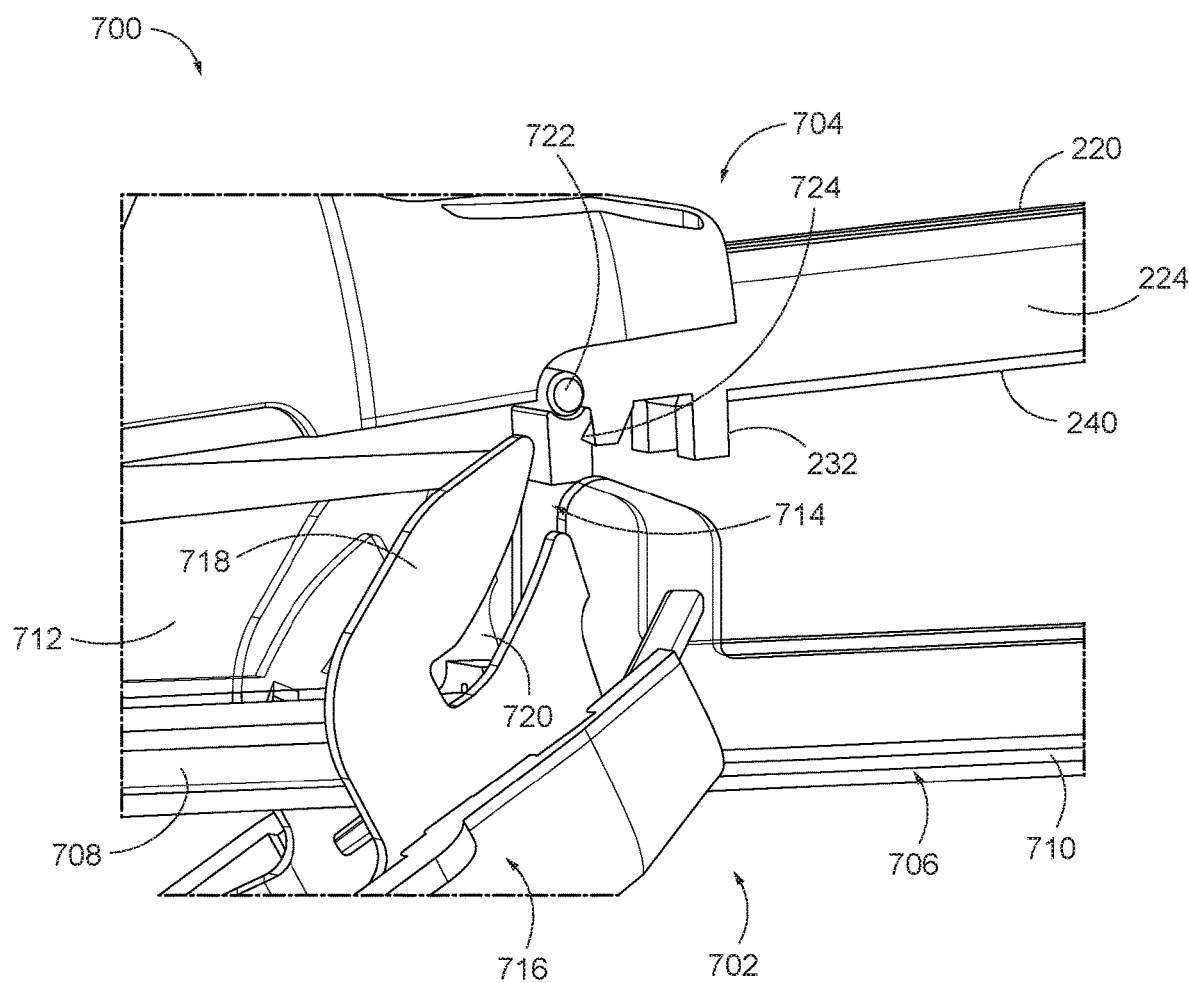
FIG. 31 depicts a perspective view of a clamping portion of another exemplary linear surgical stapler having a cartridge half and an anvil half, showing a blocking feature of the anvil half blocking premature rotation of a clamp lever of the cartridge half.

A. Exemplary Linear Surgical Stapler Having Laterally Extending Clamp Lever Blocking Feature FIG. 31 shows an exemplary linear surgical stapler (700) having a cartridge half (702) and an anvil half (704) with features similar to anvil half (200) described above, as indicated by like reference numerals. Cartridge half (702) and anvil half (704) are configured to releasably couple together to clamp tissue between distal portions thereof, similar to halves (10, 12) of stapler (10). Cartridge half (702) includes an elongate cartridge channel (706) having a proximal frame portion (708) configured to slidably house a firing assembly (not shown), and a distal jaw portion (710) configured to receive a staple cartridge (not shown). Proximal frame portion (708) includes a pair of laterally opposed side flanges (712), and a pair of vertical slots (714) arranged in the distal ends of side flanges (712). Cartridge half (702) further includes a clamp lever (716) pivotably coupled to a distal end of proximal frame portion (708). Clamp lever (716) includes a pair of laterally opposed jaws (718) (or "hook latches") each having a curved jaw slot (720) defining upper and lower camming surfaces.

In addition to the features described above in connection with FIGS. 6-13, anvil half (704) of the present example further includes a pair of latch projections defined by opposed lateral ends of a pin (722) that extends laterally through polymeric body (220) and spine plates (202, 204), shown in FIG. 7. Anvil half (704) further includes a blocking feature (724) disposed on each outer wall (222, 224) of polymeric body (220) adjacent to the respective exposed lateral end of pin (722). Each blocking feature (724) is disposed between pin (722) and a side of anvil half (704) that confronts cartridge half (702), and projects laterally outward from the respective outer wall (222, 224).

Each blocking feature (724) is formed with a sufficient lateral thickness and transverse height such that a proximal face of blocking feature (724) is configured to engage a distal tip of a respective clamp lever jaw (718) and thereby prevent clamp lever (716) from rotating toward a closed position. Specifically, blocking features (724) prevent closure of clamp lever (716) until the distal portions of stapler halves (702, 704) are approximated to the point that the opposed lateral ends of pin (722) are received within vertical slots (714) of cartridge channel (706). When stapler halves (702, 704) reach this approximated state, the opposed ends of pin (722) and blocking features (724) are disposed within vertical slots (714) and are aligned with open ends of jaw slots (720) such that clamp lever (716) may be pivoted closed. As clamp lever (716) is closed, the exposed ends of pin (722) and blocking features (724) are drawn towards closed proximal ends of jaw slots (720) via camming action, which results in anvil half (704) being clamped against cartridge half (702) to compress tissue therebetween.

B. Exemplary Linear Surgical Stapler Having Reverse Cam Feature

Figure 32:
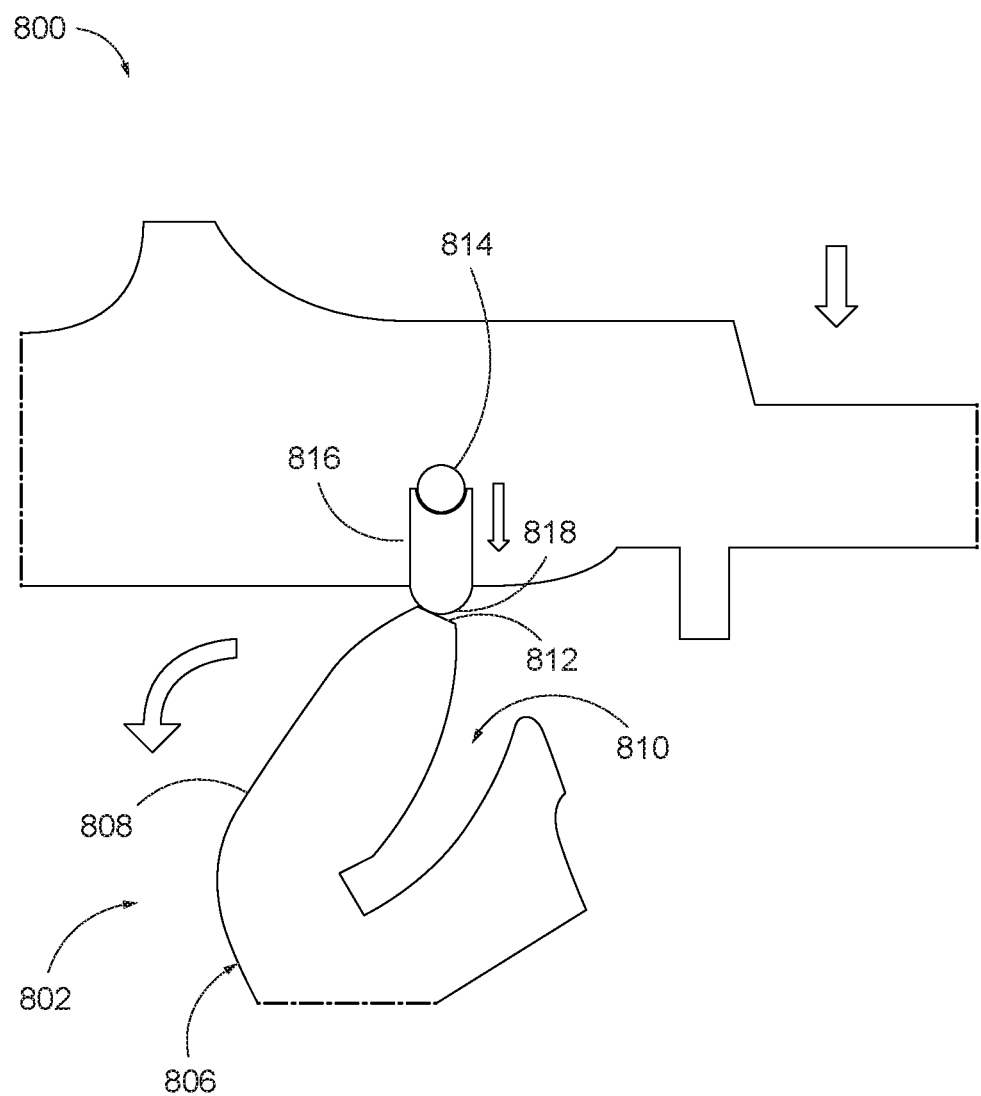
FIG. 32 depicts a perspective view of a clamping portion of another exemplary linear surgical stapler, showing a blocking feature of the anvil half interacting with a cam surface on a clamp lever of the cartridge half to automatically rotate the clamp lever into a suitable position to permit coupling of the anvil half with the cartridge half.

FIG. 32 shows another exemplary linear surgical stapler (800) having a cartridge half (802) and an anvil half (804), both shown schematically, configured to releasably couple together to clamp tissue therebetween in a manner similar to staplers (10, 700) described above. Cartridge half (802) includes a cartridge channel (not shown), which may be similar to cartridge channels (16, 706) described above, and a clamp lever (806) pivotably coupled with the cartridge channel. Clamp lever (806) includes a pair of laterally opposed jaws (808) each having a curved jaw slot (810) defining upper and lower camming surfaces. Each jaw (808)

further includes a flattened distal tip (812) configured to function as a reverse cam feature in the manner described below.

Anvil half (804) is similar in structure to anvil half (704) described above and includes a laterally extending pin (814) similar to pin (722). Anvil half (804) further includes a pair of blocking features (816) extending laterally outward from opposed lateral sides of anvil half (804) at locations adjacent to exposed lateral ends of pin (814). Each blocking feature (816) includes a rounded tip (818) configured to cam against the flattened distal tip (812) of the respective clamp lever jaw (808) to thereby urge clamp lever (806) toward an open position during approximation of stapler halves (802, 804). Additionally, similar to blocking features (724) described above, blocking features (816) are suitably sized and shaped to block clamp lever (806) from pivoting closed until distal portions of stapler halves (802, 804) are sufficiently approximated so that pin (722) is received into vertical slots (not shown) of the cartridge channel, similar to vertical slots (714) of cartridge channel (706) described above.

V. Exemplary Method of Forming Anvil Pockets

Figure 35A:
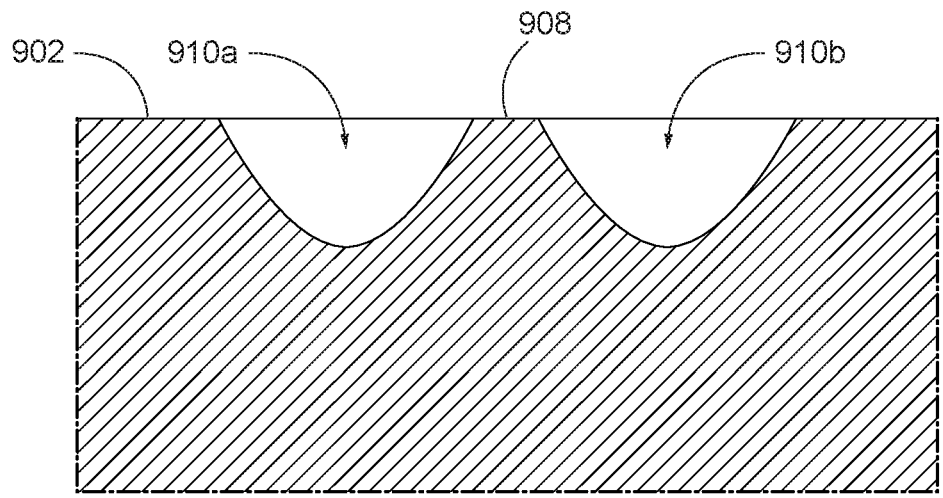
FIG. 35A depicts a cross-sectional view of the portion of the anvil plate of FIG. 33, taken along section line 35A-35A, showing initial recesses formed in the anvil plate after completion of a first step of the pocket formation process.
Figure 35B:
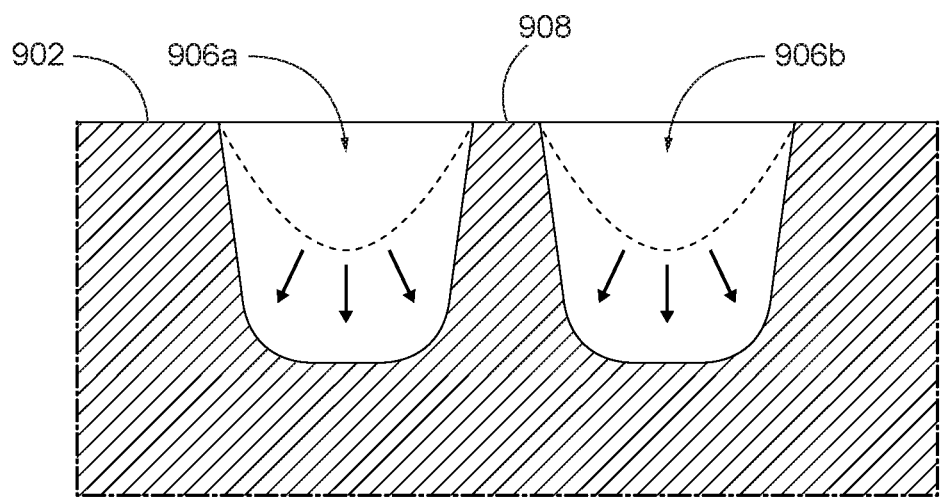
FIG. 35B depicts a cross-sectional view of the portion of the anvil plate of FIG. 33, taken along section line 35A-35A, showing final pocket shapes formed in the anvil plate after completion of a second step of the pocket formation process.

Traditionally, the staple-forming pockets on the anvil surface of a surgical stapler are formed through a single-step process, such as precision stamping (or "coining"). In some instances, however, it may be desirable to form the pockets of an anvil surface in multiple steps. FIGS. 35A-35B show steps of an exemplary process that implements first and second steps for forming pockets in an anvil surface, as described in detail below. In the present example, the anvil surface is shown in the form of an anvil plate (900) that is attachable to a body structure of a corresponding anvil half, such as polymeric bodies (220, 320, 420) of anvil halves (200, 300, 400) described above. In other examples, the anvil surface in which the pockets are formed may be provided by the body structure itself.

Figure 33:
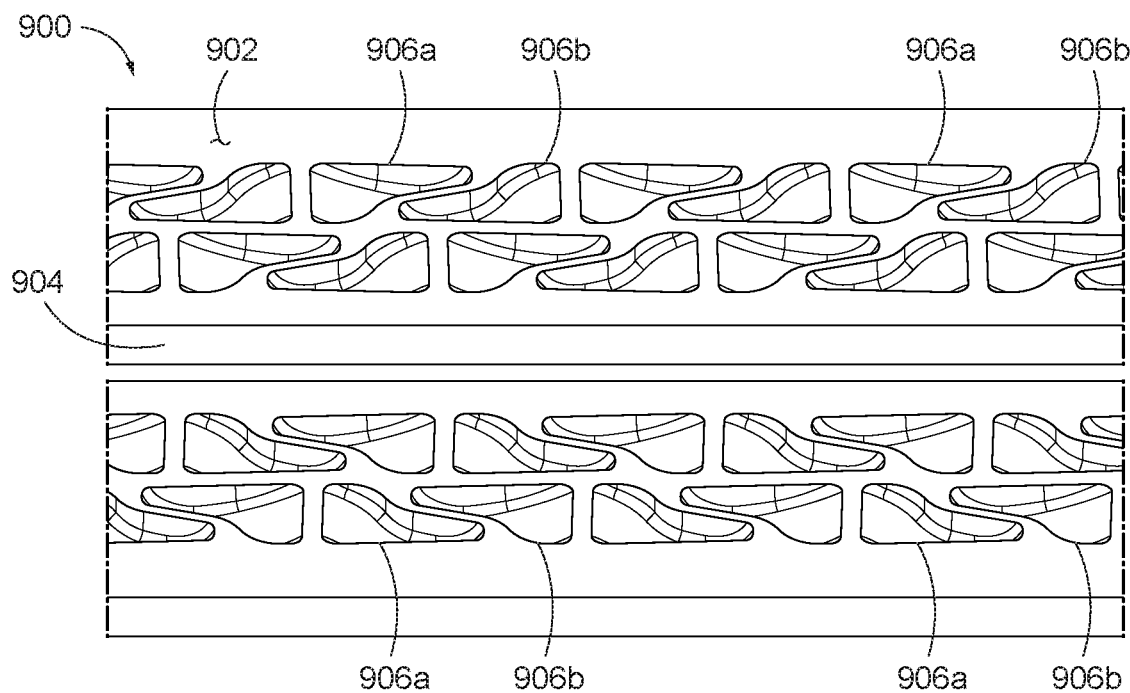
FIG. 33 depicts a top perspective view of an exemplary anvil plate having a plurality of anvil pockets formed by an exemplary two-step pocket formation process.

FIG. 33 shows a medial portion of an exemplary anvil plate (900) suitable for use with the anvil half of a linear surgical stapler, such as any of the exemplary anvil halves (200, 300, 400, 704, 804) described above. Anvil plate (900) includes a top surface (902), a longitudinal slot (904) extending through top surface (902) and opening to a bottom surface (not shown) of anvil plate (900), and a plurality of staple-forming pockets (or "anvil pockets") (906a, 906b) formed in top surface (902) along both lateral sides of longitudinal slot (904). Longitudinal slot (904) is configured to slidably receive a knife member of a firing assembly, such as knife (616) of firing assembly (600) described above.

Figure 34:
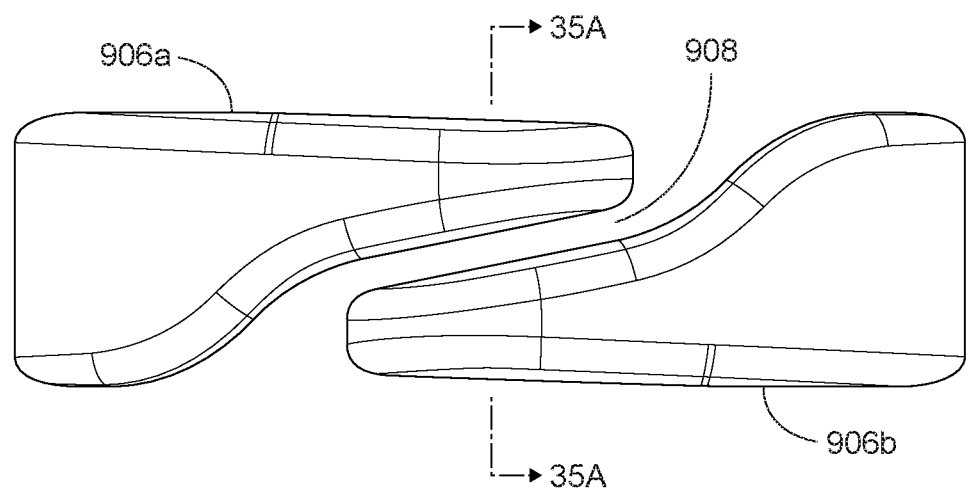
FIG. 34 depicts an enlarged top plan view of a pair of anvil pockets of the anvil plate of FIG. 33.

As shown in FIGS. 33 and 34, anvil pockets (906a, 906b) are formed with a similar shape, and anvil pockets (906a) are oriented in a first direction while anvil pockets (906b) are oriented in an opposed second direction. Accordingly, each pair of pockets (906a, 906b) is configured to cooperate to deform a respective staple (not shown) ejected by a staple cartridge. As shown best in FIG. 34, this arrangement of anvil pockets (906a, 906b) results in each pair of anvil pockets (906a, 906b) being provided in complimentary orientations such that a tapered portion of pocket (906a) extends alongside a tapered portion of pocket (906b) to define a sidewall (908) therebetween.

FIG. 35A shows a first step of an exemplary process for forming anvil pockets (906a, 906b) in anvil plate (900), in which a first manufacturing method is implemented to create initial recesses (910a, 910b) in top surface (902) of anvil plate (900). The first manufacturing method may comprise electrical discharge machining (EDM) or electrochemical machining (ECM), for example. FIG. 35B shows a second step of the exemplary pocket forming process in which a second, different manufacturing method is implemented to deepen initial recesses (910a, 910b) and thereby transform recesses (910a, 910b) into respective final pockets (906a, 906b). The second manufacturing method may be in the form of coining, for example. In the present version, an entirety of each initial recess (910a, 910b) is acted upon by the second manufacturing method to yield the final pocket (906a, 906b).

As shown in FIGS. 35A-35B, the exemplary two-step process described above yields precisely formed anvil pockets (906a, 906b) having a sidewall (908) therebetween whose shape and integrity is not substantially compromised during pocket formation. As a result, the final sidewall (908) does not exhibit degradation (or "pull-down") in which an upper surface of sidewall (908) becomes recessed beneath top surface (902) of anvil plate (900) during pocket formation, which can yield suboptimal formation of staples during use. Thus, this mitigation of sidewall "pull-down" through the process described above enables anvil pockets (906a, 906b) to form optimally shaped staples consistently during use. In various applications, the above-described process is effective to produce anvil pockets (906a, 906b) having a depth of greater than or equal to approximately 0.014 inches, and a sidewall (908) having a lateral thickness of less than or equal to approximately 0.010 inches, while minimizing pull-down of sidewall (908). Other advantages of the exemplary pocket forming process described above include reduced stress on manufacturing tooling, minimized use of expensive machining processes such as ECM, and ability to form anvil plate (900) from harder materials as compared to pocket formation processes that implement a single manufacturing step.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapler comprising: (a) a first stapler half; and (b) a second stapler half configured to releasably couple with the first stapler half, wherein the second stapler half comprises: (i) a first elongate member, (ii) a second elongate member, and (iii) a polymeric body, wherein the polymeric body encapsulates at least a portion of each of the first elongate member and the second elongate member, wherein one of the first stapler half or the second stapler half includes a distal portion configured to receive a staple cartridge, wherein the other of the first stapler half or the second stapler half includes a distal portion having a plurality of staple-forming pockets.

Example 2

The surgical stapler of Example 1, wherein the first and second elongate members are parallel to one another.

Example 3

The surgical stapler of any of the preceding Examples, wherein the first and second elongate members are spaced laterally from one another.

Example 4

The surgical stapler of any of the preceding Examples, wherein the first and second elongate members are the same length.

Example 5

The surgical stapler of any of the preceding Examples, wherein the first elongate member comprises a first plate, wherein the second elongate member comprises a second plate.

Example 6

The surgical stapler of any of the preceding Examples, wherein the staple-forming pockets are arranged on an anvil surface, wherein the anvil surface is oriented transversely to the first plate and the second plate.

Example 7

The surgical stapler of any of the preceding Examples, wherein each of the first and second elongate members comprises a non-polymeric material.

Example 8

The surgical stapler of any of the preceding Examples, wherein at least one of the first elongate member or the second elongate member includes a raised portion that extends transversely away from the staple-forming pockets.

Example 9

The surgical stapler of any of the preceding Examples, wherein each of the first and second elongate members tapers distally.

Example 10

The surgical stapler of any of the preceding Examples, wherein the first and second elongate members are connected by an adjoining member, wherein the adjoining member is formed integrally with the first and second elongate members.

Example 11

The surgical stapler of any of the preceding Examples, wherein the first elongate member includes a projection that extends transversely to a longitudinal axis of the first elongate member, wherein the second elongate member includes an opening that receives the projection.

Example 12

The surgical stapler of any of the preceding Examples, wherein the first elongate member includes a plurality of first openings, wherein the second elongate member includes a plurality of second openings, wherein the polymeric body extends into each of the first openings and the second openings.

Example 13

The surgical stapler of any of the preceding Examples, wherein the polymeric body extends for a full length of the first elongate member and the second elongate member.

Example 14

The surgical stapler of any of the preceding Examples, wherein the polymeric body defines a tapered distal tip of the second stapler half.

Example 15

The surgical stapler of any of the preceding Examples, further comprising an anvil plate secured to the polymeric body, wherein the anvil plate defines the plurality of staple-forming pockets.

Example 16

A surgical stapler comprising: (a) a first stapler half having a distal portion configured to receive a staple cartridge; and (b) a second stapler half configured to releasably couple with the first stapler half, wherein the second stapler half comprises: (i) a first elongate member, (ii) a second elongate member, (iii) a polymeric body, wherein the polymeric body spans between the first elongate member and the second elongate member, wherein the polymeric body extends along an exterior surface of each of the first elongate member and the second elongate member, and (iv) a plurality of staple-forming pockets arranged on a distal portion of the second stapler half.

Example 17

The surgical stapler of Example 16, wherein the polymeric body couples the first elongate member with the second elongate member.

Example 18

The surgical stapler of any of Examples 16 through 17, wherein the first elongate member comprises a first plate, wherein the second elongate member comprises a second plate.

Example 19

A method of making a portion of a surgical stapler, the method comprising: (a) positioning a first elongate member within a mold; (b) positioning a second elongate member within the mold adjacent to the first elongate member; (c) positioning an anvil plate within the mold transversely relative to the first elongate member and the second elongate member, wherein the anvil plate includes a plurality of staple-forming pockets; and (d) injecting a polymeric material into the mold such that the polymeric material forms a body that encapsulates at least a portion of each of the first elongate member and the second elongate member, wherein the body is coupled to the anvil plate.

Example 20

The surgical stapler of Example 19, wherein positioning the second elongate member adjacent to the first elongate member comprises positioning the second elongate member parallel to the first elongate member.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/889,363, entitled "Release Mechanism for Linear Surgical Stapler," filed on Feb. 6, 2018, issued as U.S. Pat. No. 10,631,866 on Apr. 28, 2020; U.S. application Ser. No. 15/889,370, entitled "Lockout Assembly for Linear Surgical Stapler," filed on Feb. 6, 2018, issued as U.S. Pat. No. 10,667,818 on Jun. 2, 2020; U.S. application Ser. No. 15/889,374, entitled "Features to Align and Close Linear Surgical Stapler," filed on Feb. 6, 2018, issued as U.S. Pat. No. 10,932,781 on Mar. 2, 2021; U.S. application Ser. No. 15/889,376, entitled "Releasable Coupling Features for Proximal Portions of Linear Surgical Stapler," filed on Feb. 6, 2018, issued as U.S. Pat. No. 10,898,197 on Jan. 26, 2021; U.S. application Ser. No. 15/889,388, entitled "Firing Lever Assembly for Linear Surgical Stapler," filed on Feb. 6, 2018, issued as U.S. Pat. No. 10,874,398 on Dec. 29, 2020; U.S. application Ser. No. 15/889,390, entitled "Clamping Mechanism for Linear Surgical Stapler," filed on Feb. 6, 2018, issued as U.S. Pat. No. 10,687,819 on Jun. 23, 2020; U.S. application Ser. No. 16/102,164, entitled "Firing System for Linear Surgical Stapler," filed on Aug. 13, 2018, issued as U.S. Pat. No. 10,898,187 on Jan. 26, 2021; U.S. application Ser. No. 16/102,170, entitled "Clamping Assembly for Linear Surgical Stapler," filed on Aug. 13, 2018, published as U.S. Pub. No. 2020/0046353 on Feb. 13, 2020; and U.S. App. Ser. No. 16/157,605, entitled "Closure Assembly for Linear Surgical Stapler," filed on Oct. 11, 2018, issued as U.S. Pat. No. 10,905,419 on Feb. 2, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapler comprising:
   (a) a first stapler half; and
   (b) a second stapler half configured to releasably couple with the first stapler half, wherein the second stapler half comprises:
      (i) a first elongate member,
      (ii) a second elongate member, wherein a proximal end of each of the first and second elongate members coincides with a proximal end of the second stapler half, and
      (iii) a polymeric body, wherein the polymeric body encapsulates at least a portion of each of the first elongate member and the second elongate member,
   wherein the first stapler half includes a distal portion defining a first stapling surface,
   wherein the second stapler half includes a distal portion defining a second stapling surface configured to cooperate with the first stapling surface to compress and staple tissue.

2. The surgical stapler of claim 1, wherein the first and second elongate members are parallel to one another.

3. The surgical stapler of claim 1, wherein the first and second elongate members are spaced laterally from one another.

4. The surgical stapler of claim 1, wherein the first and second elongate members are of the same length.

5. The surgical stapler of claim 1, wherein the first elongate member comprises a first plate, wherein the second elongate member comprises a second plate.

6. The surgical stapler of claim 5, wherein one of the first stapling surface or the second stapling surface comprises an anvil surface having a plurality of staple forming pockets, wherein the anvil surface is oriented transversely to the first plate and the second plate.

7. The surgical stapler of claim 1, wherein each of the first and second elongate members comprises a non-polymeric material.

8. The surgical stapler of claim 1, wherein at least one of the first elongate member or the second elongate member includes a raised portion that extends transversely away from the first and second stapling surfaces.

9. The surgical stapler of claim 1, wherein each of the first and second elongate members tapers distally.

10. The surgical stapler of claim 1, wherein the first and second elongate members are connected by an adjoining member, wherein the adjoining member is formed integrally with the first and second elongate members.

11. The surgical stapler of claim 1, wherein the first elongate member includes a projection that extends transversely to a longitudinal axis of the first elongate member, wherein the second elongate member includes an opening that receives the projection.

12. The surgical stapler of claim 1, wherein the first elongate member includes a plurality of first openings, wherein the second elongate member includes a plurality of second openings, wherein the polymeric body extends into each of the first openings and the second openings.

13. The surgical stapler of claim 1, wherein the polymeric body extends for a full length of the first elongate member and the second elongate member.

14. The surgical stapler of claim 1, wherein the polymeric body defines a tapered distal tip of the second stapler half.

15. The surgical stapler of claim 1, wherein the second stapling surface comprises an anvil plate secured to the polymeric body, wherein the anvil plate defines a plurality of staple-forming pockets.

16. A surgical stapler comprising:
   (a) a first stapler half having a distal portion configured to receive a staple cartridge; and
   (b) a second stapler half configured to releasably couple with the first stapler half, wherein the second stapler half comprises:
      (i) a first elongate member, (ii) a second elongate member, (iii) a polymeric body, wherein the polymeric body spans between the first elongate member and the second elongate member, wherein a proximal end of the polymeric body coincides with a proximal end of the second stapler half, and a distal end of the polymeric body coincides with a distal end of the second stapler half, and (iv) a plurality of staple-forming pockets arranged on a distal portion of the second stapler half.

17. The surgical stapler of claim 16, wherein the polymeric body couples the first elongate member with the second elongate member.

18. The surgical stapler of claim 16, wherein the first elongate member comprises a first plate, wherein the second elongate member comprises a second plate.

19. A surgical stapler comprising:
(a) a first stapler portion having a first stapling surface; and
(b) a second stapler portion configured to releasably couple with the first stapler portion, wherein the second stapler portion comprises:
(i) an elongate member,
(ii) a polymeric body that encapsulates at least a portion of the elongate member, wherein each of the elongate member and the polymeric body includes a proximal end that coincides with a proximal end of the second stapler portion, and
(iii) a second stapling surface configured to cooperate with the first stapling surface to compress and staple tissue.

20. The surgical stapler of claim 19, wherein the elongate member comprises a first plate, wherein the second stapler portion further comprises a second plate that extends parallel to the first plate and is at least partially encapsulated by the polymeric body.

* * * * *